(12) United States Patent
Rhodes et al.

(10) Patent No.: US 9,777,333 B2
(45) Date of Patent: Oct. 3, 2017

(54) GENE FUSION

(71) Applicant: LIFE TECHNOLOGIES CORPORATION, Carlsbad, CA (US)

(72) Inventors: Daniel Rhodes, Ann Arbor, MI (US); Seth Sadis, Ann Arbor, MI (US); Peter Wyngaard, Ann Arbor, MI (US); Armand Bankhead, Britton, MI (US); Dinesh Cyanam, Ypsilanti, MI (US); Nikolay Khazanov, Ann Arbor, MI (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 14/244,824

(22) Filed: Apr. 3, 2014

(65) Prior Publication Data
US 2014/0323329 A1  Oct. 30, 2014

Related U.S. Application Data

(60) Provisional application No. 61/809,252, filed on Apr. 5, 2013.

(51) Int. Cl.
*C12Q 1/68* (2006.01)
*C07H 21/02* (2006.01)

(52) U.S. Cl.
CPC ..... *C12Q 1/6886* (2013.01); *C12Q 2600/156* (2013.01)

(58) Field of Classification Search
CPC ................. C12C 1/6886; C12C 2600/156
See application file for complete search history.

(56) References Cited

U.S. PATENT DOCUMENTS

2015/0031703 A1* 1/2015 Suzuki ................ C12Q 1/6886
514/252.12

FOREIGN PATENT DOCUMENTS

| WO | WO-2011/087709 | 7/2011 |
| WO | WO-2013/133351 | 9/2013 |
| WO | WO-2014/071419 | 5/2014 |

OTHER PUBLICATIONS

Singh, D. et al., Science, vol. 337, pp. 1231-1235 (2012).*
Longo, M.C. et al., Gene, vol. 93, pp. 125-128 (1990).*
GeneCards entry for CCDC6 (downloaded from www.genecards.org/cgi-bin/carddisp.pl?gene=CCDC6 Oct. 15, 2016).*
Bhaijee, F. et al., "New developments in the molecular pathogenesis of head and neck tumors: a review of tumor-specific fusion oncogenes in mucoepidermoid carcinoma, adenoid cystic carcinoma, and NUT midline carcinoma", *Annals of Diagnostic Pathology*, vol. 15 (1), Feb. 1, 2011, 69-77.
Chinnaiyan, A. et al., "Chromosomal Aberrations in Solid Tumors", *Progress in Molecular Biology and Translational Science*, vol. 95, Jan. 1, 2010, 55-94.
Majewski, I. et al., "Identification of Recurrent FGFR3 Fusion Genes in Lung Cancer Through Kinome-Centred RNA Sequencing", *Journal of Pathology*, vol. 230, Jul. 7, 2013, 270-276.
Parker, B. et al., "The tumorigenic FGFR3-TACC3 gene fusion escapes miR-99a regulation in glioblastoma", *Journal of Clinical Investigation*, vol. 123 (2), Feb. 1, 2013, 855-865.
PCT/US2014/032888, "International Search Report mailed Dec. 8, 2015", Dec. 8, 2015, 12.
Singh, D. et al., "Transforming Fusions of FGFR and TACC Genes in Human Glioblastoma", *Science*, vol. 337, Sep. 7, 2012, 1231-1235.
Williams, S. et al., "Oncogenic FGFR3 Gene Fusions in Bladder Cancer", *Human Molecular Genetics*, vol. 22 (4), Nov. 21, 2012, 795-803.
WO201313335, Machine Translation, "Novel FGFR3 Fusion Product", *WIPO Patentscope: Google Translation of WO201313335 into English*, Sep. 12, 2013.
Wu, Y-M et al., "Identification of Targetable FGFR Gene Fusions in Diverse Cancers", *Cancer Discovery*, vol. 3 (6), Apr. 4, 2013, 636-647.
*Discovery*, vol. 3 (6), Apr. 4, 2013, 636-647.

* cited by examiner

*Primary Examiner* — Teresa Strzelecka

(57) ABSTRACT

The disclosure provides gene fusion variants and novel associations with disease states, as well as kits, probes, and methods of using the same.

9 Claims, 18 Drawing Sheets

Gene Fusion Processing Workflows

| TCGA Tumor Sample Barcode | GeneA Gene Symbol | GeneA Chromosome | GeneA Breakpoint |
|---|---|---|---|
| TCGA-CH-5739-01A-11R-1580-07 | TMPRSS2 | chr21 | 42,879,877 |
| TCGA-CH-5740-01A-11R-1580-07 | TMPRSS2 | chr21 | 42,870,046 |
| TCGA-CH-5741-01A-11R-1580-07 | TMPRSS2 | chr21 | 42,870,046 |
| TCGA-CH-5746-01A-11R-1580-07 | TMPRSS2 | chr21 | 42,879,877 |
| TCGA-CH-5765-01A-11R-1580-07 | TMPRSS2 | chr21 | 42,879,877 |
| TCGA-CH-5768-01A-11R-1580-07 | TMPRSS2 | chr21 | 42,879,877 |
| TCGA-CH-5769-01A-11R-1580-07 | TMPRSS2 | chr21 | 42,870,046 |
| TCGA-CH-5789-01A-11R-1580-07 | TMPRSS2 | chr21 | 42,866,283 |
| TCGA-CH-5790-01A-11R-1580-07 | TMPRSS2 | chr21 | 42,879,891 |
| TCGA-EJ-5496-01A-01R-1580-07 | TMPRSS2 | chr21 | 42,879,884 |
| TCGA-EJ-5497-01A-02R-1580-07 | TMPRSS2 | chr21 | 42,870,046 |
| TCGA-EJ-5499-01A-01R-1580-07 | TMPRSS2 | chr21 | 42,870,046 |
| TCGA-EJ-5507-01A-01R-1580-07 | TMPRSS2 | chr21 | 42,880,008 |
| TCGA-EJ-5508-01A-02R-1580-07 | TMPRSS2 | chr21 | 42,880,008 |
| TCGA-EJ-5516-01A-01R-1580-07 | TMPRSS2 | chr21 | 42,880,008 |
| TCGA-EJ-5522-01A-01R-1580-07 | TMPRSS2 | chr21 | 42,879,877 |
| TCGA-EJ-5524-01A-01R-1580-07 | TMPRSS2 | chr21 | 42,879,891 |
| TCGA-EJ-5525-01A-01R-1580-07 | TMPRSS2 | chr21 | 42,870,046 |
| TCGA-EJ-5526-01A-01R-1580-07 | TMPRSS2 | chr21 | 42,870,046 |
| TCGA-EJ-5542-01A-01R-1580-07 | TMPRSS2 | chr21 | 42,866,406 |
| TCGA-G9-6332-01A-11R-1789-07 | TMPRSS2 | chr21 | 42,870,046 |
| TCGA-G9-6365-01A-11R-1789-07 | TMPRSS2 | chr21 | 42,870,046 |
| TCGA-G9-6384-01A-11R-1789-07 | TMPRSS2 | chr21 | 42,879,877 |

TMRSS2 | ERG Observed in 57% of Prostate Samples

FIG. 5A1

| GeneB Gene Symbol | GeneB Chromosome | GeneB Breakpoint | Spanning Reads | Fusion Exon |
|---|---|---|---|---|
| ERG | chr21 | 39,817,544 | 30 | T2-E4 |
| ERG | chr21 | 39,817,544 | 59 | T3-E4 |
| ERG | chr21 | 39,817,544 | 198 | T3-E4 |
| ERG | chr21 | 39,817,544 | 10 | T2-E4 |
| ERG | chr21 | 39,817,544 | 9 | T2-E4 |
| ERG | chr21 | 39,956,869 | 17 | T2-E1 |
| ERG | chr21 | 39,817,544 | 42 | T3-E4 |
| ERG | chr21 | 39,817,544 | 54 | T4-E4 |
| ERG | chr21 | 39,817,518 | 23 | T2-E2 |
| ERG | chr21 | 39,870,288 | 23 | T2-E4 |
| ERI | chr21 | 39,817,544 | 52 | T3-E4 |
| ERG | chr21 | 39,817,544 | 75 | T3-E4 |
| ERG | chr21 | 39,817,544 | 5 | T1-E4 |
| ERG | chr21 | 39,817,544 | 8 | T1-E4 |
| ERG | chr21 | 39,817,544 | 5 | T1-E4 |
| ERG | chr21 | 39,956,869 | 25 | T2-E2 |
| ERG | chr21 | 39,817,518 | 30 | T2-E4 |
| ERG | chr21 | 39,817,544 | 61 | T3-E4 |
| ERG | chr21 | 39,817,544 | 188 | T3-E4 |
| ERG | chr21 | 39,817,479 | 6 | T4-E4 |
| ERG | chr21 | 39,817,544 | 214 | T3-E4 |
| ERG | chr21 | 39,817,544 | 15 | T3-E4 |
| ERG | chr21 | 39,817,544 | 33 | T2-E4 |

TMRSS2 | ERG Observed in 57% of Prostate Samples

FIG. 5A2

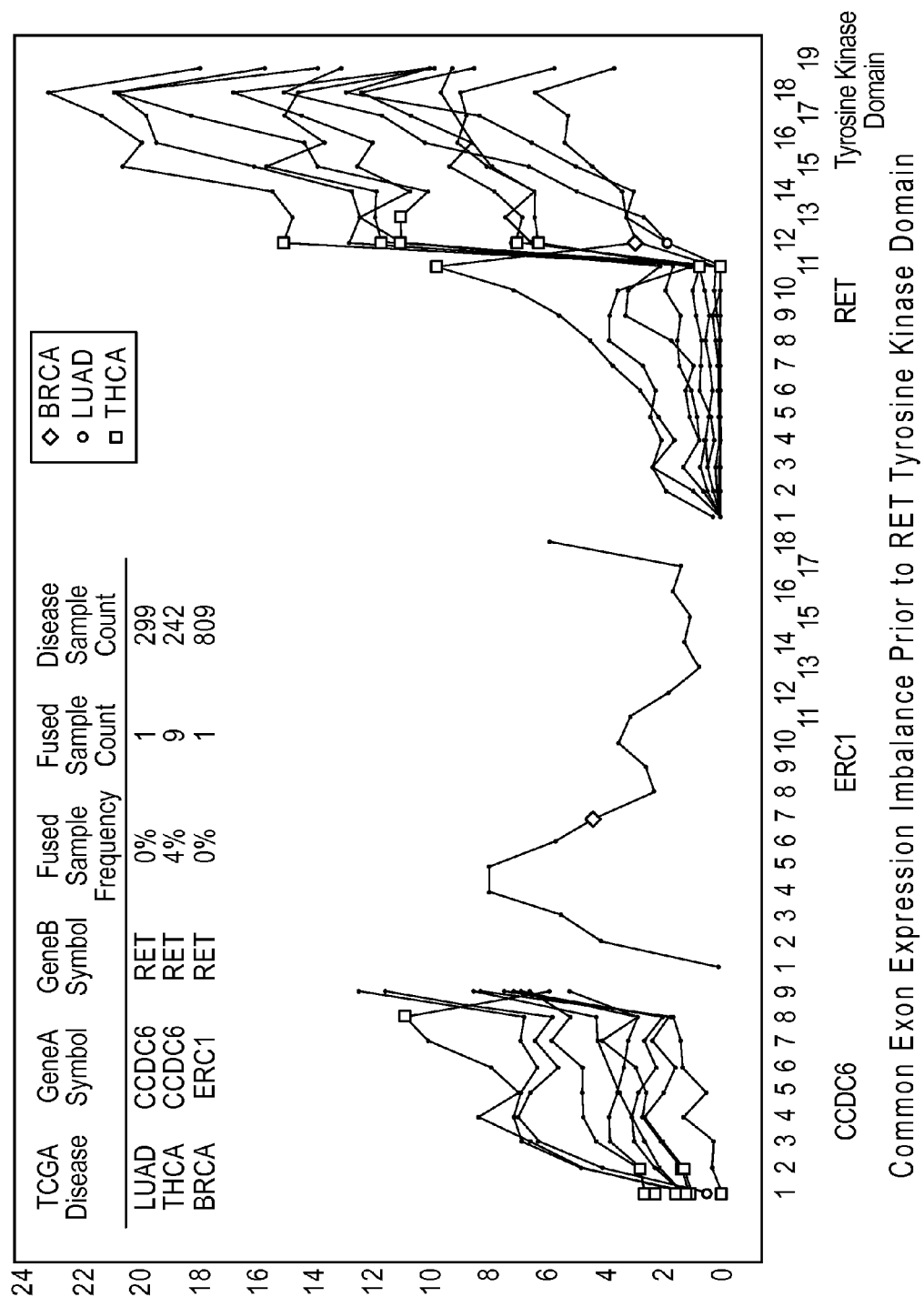

GENE FUSION

RELATED APPLICATIONS

This application claims priority to U.S. Provisional Patent Application 61/809,252, filed on Apr. 5, 2013, which disclosure is incorporated by reference in its entirety.

SEQUENCE LISTING

The instant application contains a Sequence Listing which has been submitted electronically in ASCII format and is hereby incorporated by reference in its entirety. Said ASCII copy, created on Jun. 17, 2014, is named LT00811_SL.txt and is 2,996 bytes in size.

BACKGROUND

Chromosomal aberrations such as translocations are frequently found in human cancer cells. Chromosomal translocations may result in a chimeric gene expressing a fusion transcript which is then translated into a fusion protein that affects normal regulatory pathways and stimulates cancer cell growth.

The identification of new fusion genes or new variants of known fusion genes provides an opportunity for additional diagnostics and cancer treatment targets.

BRIEF SUMMARY

The disclosure provides novel gene fusion variants and gene fusion-disease state associations. The gene fusions provided herein are associated with certain cancers. The disclosure further provides probes, such as amplification primer sets and detection probes, as well as methods of detection, diagnosis, and treatment and kits that include or detect the gene fusions disclosed herein.

In one embodiment, the disclosure provides a composition and a kit comprising a set of probes that specifically recognize a gene fusion of FGFR3 and TACC3. The set of probes can be, for example a set of amplification primers. In another embodiment, provided herein is a composition that includes a set of primers that flank an FGFR3 and TACC3 breakpoint in a target nucleic acid. The reaction mixture of this embodiment can further include a detector probe that binds to either side of the FGFR3 and TACC3 breakpoint, or that binds a binding region that spans the FGFR3 and TACC3 breakpoint. The reaction mixture that includes a detector probe or does not include a detector probe, can further include a polymerase, dNTPS, and/or a uracil DNA deglycosylase (UDG). The polymerase and UDG are typically not from a human origin. The reaction mixture can further include a target nucleic acid, for example a human target nucleic acid. The human target nucleic acid can be, for example, isolated from a biological sample from a person suspected of having bladder, head and neck, or lung squamous cell carcinoma.

In another embodiment, a set of probes that specifically recognize a nucleic acid comprising at least one of SEQ ID NOs: 1-12 is provided. In another embodiment, provided herein is a set of primers that specifically amplify a target nucleic acid that includes SEQ ID NOs: 1-12. In another embodiment, provided herein is a qPCR assay, such as a TaqMan assay or a Molecular Beacons assay, that specifically amplifies and detects a target nucleic acid that includes SEQ ID NOs: 1-12.

The disclosure also provides an isolated nucleic acid comprising at least one sequence selected from SEQ ID NOs: 1-12. The isolated nucleic acid can include a first primer on a 5' end. Furthermore, the nucleic acid can be single stranded or double stranded.

The disclosure, in other embodiments, provides a kit that includes a detector probe and/or a set of probes, for example, a set of amplification primers that specifically recognize a nucleic acid comprising an FGFR3 and TACC3 breakpoint. For example, in certain embodiments the detector probe or set of amplification primers are designed to amplify and/or detect a nucleic acid that include SEQ ID NOs: 1-12. The kit can further include, in a separate or in the same vessel, a component from an amplification reaction mixture, such as a polymerase, typically not from human origin, dNTPs, and/or UDG. Furthermore, the kit can include a control nucleic acid. For example the control nucleic acid can include a sequence that includes the break point from Table 3.

A method of detecting bladder, head and neck, or lung squamous cell carcinoma is provided comprising amplifying a nucleic acid that spans an FGFR3 and TACC3 breakpoint, for example the nucleic can include a sequence selected from SEQ ID NOs: 1-12, and detecting the presence of the nucleic acid, wherein the presence of the nucleic acid indicates bladder, head and neck, or lung squamous cell carcinoma is present in the sample. In another method, provided herein is a method of detecting bladder, head and neck, or lung squamous cell carcinoma that includes generating an amplicon that includes a sequence selected from SEQ ID NOs: 1-12, and detecting the presence of the nucleic acid, wherein the presence of the nucleic acid indicates bladder, head and neck, or lung squamous cell carcinoma is present in the sample. The amplicon typically includes primers that are extended to form the amplicon.

A kit comprising a set of probes, for example, a set of amplification primers that specifically recognize a nucleic acid comprising a break point from Table 3 is provided. The kit can further include, in a separate or in the same vessel, a component from an amplification reaction mixture, such as a polymerase, typically not from human origin, dNTPs, and/or UDG. Furthermore, the kit can include a control nucleic acid. For example the control nucleic acid can include a sequence that includes the break point from Table 3.

In certain embodiments, a set of probes that specifically recognize a nucleic acid comprising a break point from Table 3 is provided.

In another embodiment, a gene fusion is provided comprising at least one of the break points in Table 3.

In another embodiment is a method to detect lung squamous cell carcinoma or thyroid carcinoma in a sample by detecting the presence of a CCDC6/RET gene fusion.

In yet another embodiment, the disclosure provides a method of detecting breast carcinoma in a sample by detecting the presence of an ERC1/RET gene fusion.

DESCRIPTION OF THE DRAWINGS

FIG. 5A1-5A2 shows defuse breakpoint calls for each of the 23 fusion positive patients.

FIG. 9 is a graph showing gene fusions involving RET observed with multiple partners (e.g. CCDC6 and ERC1) across thyroid, lung squamous and breast carcinomas. Breakpoints were observed at similar locations within RET and CCDC6 fusion partners.

Definitions

Figure 1:
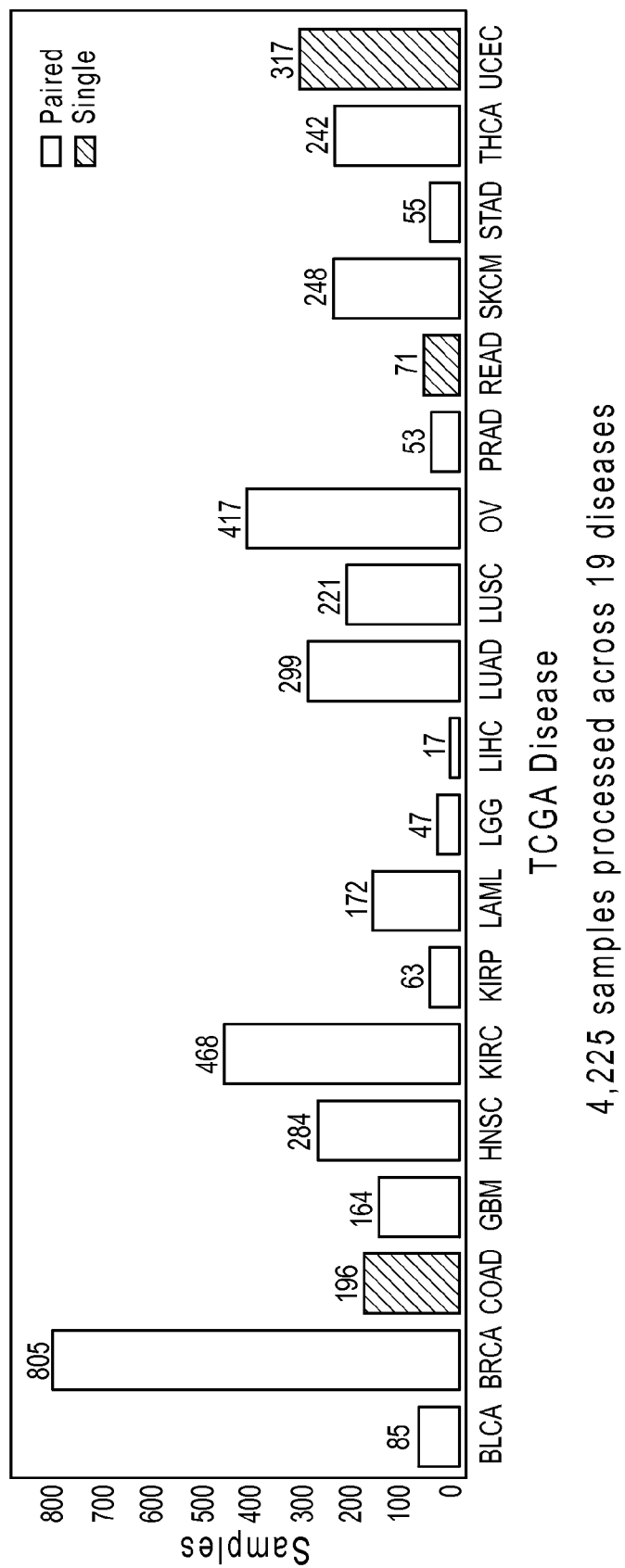
FIG. 1 is a chart showing the number of samples processed per disease state. 4,225 samples were processed across 19 diseases with defuse and tophat gene fusion calling software using cloud-based computing.
Figure 2:
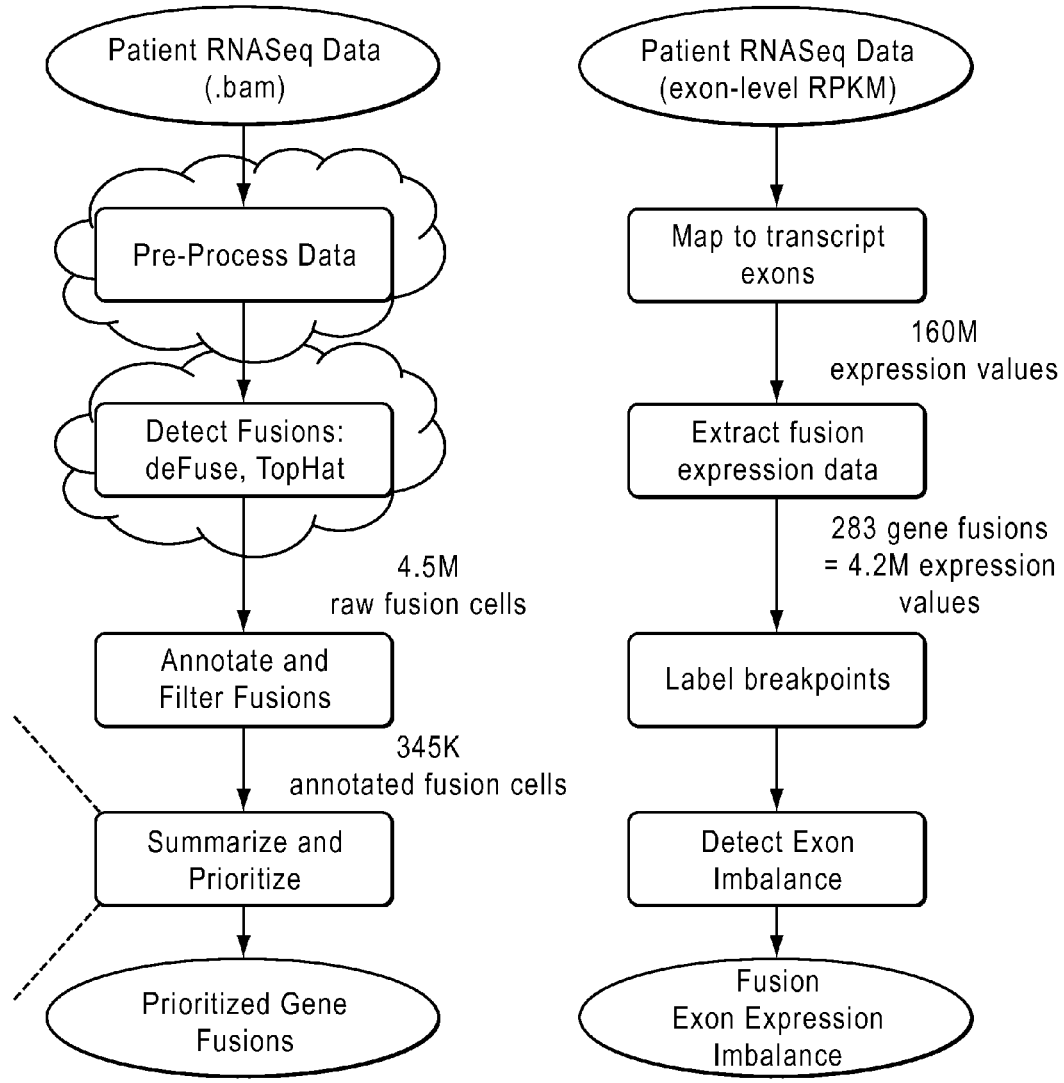
FIG. 2 provides 2 gene fusion processing work flows. Gene fusion processing produced 4.5 million calls that were filtered and prioritized to generate a list of high confidence "priority" fusion calls.
Figure 3:
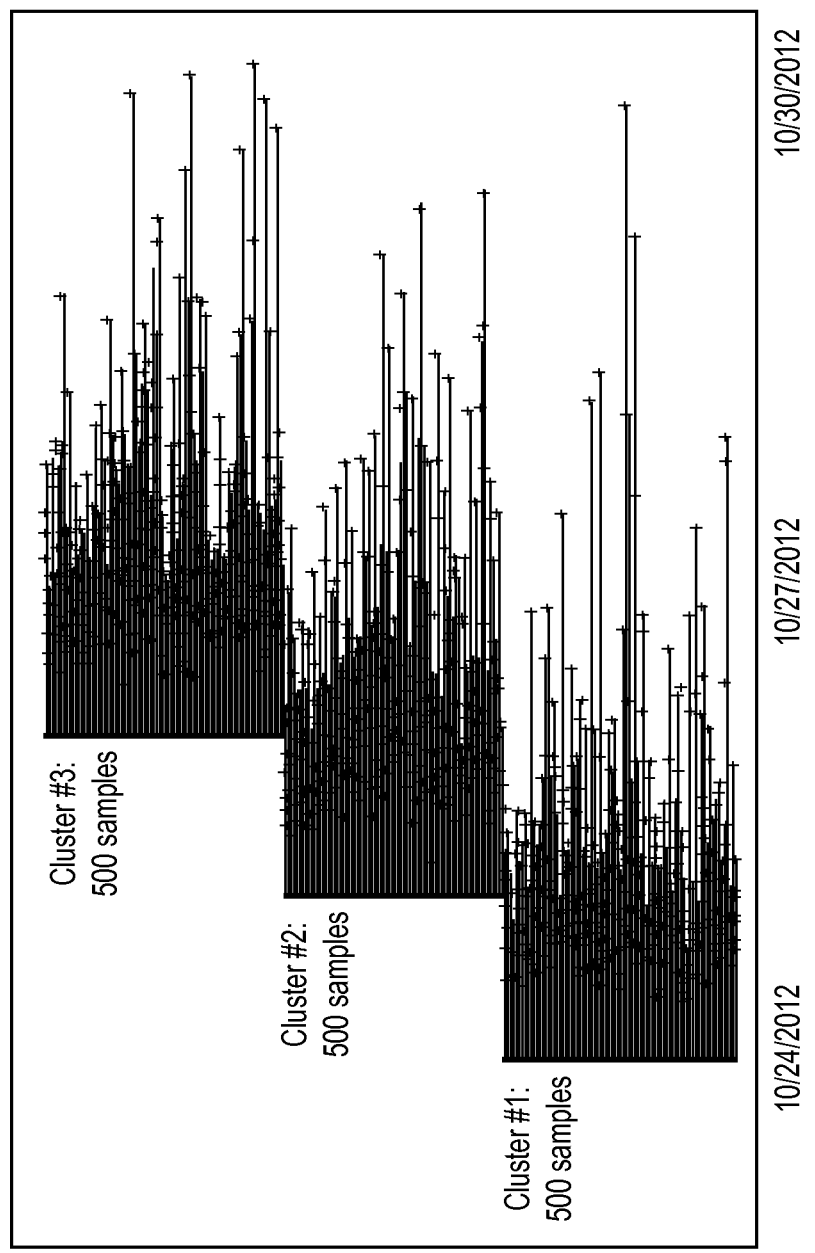
FIG. 3 shows gene fusion detection using cluster computing: 4.65 compute years in 6 days. Three 500 node clusters were used to process samples using defuse caller software. In total, 4,225 RNASeq samples were processed generating 28.2 TB of fusion results data.

The term "marker" or "biomarker" refers to a molecule (typically protein, nucleic acid, carbohydrate, or lipid) that is expressed in the cell, expressed on the surface of a cancer cell or secreted by a cancer cell in comparison to a non-cancer cell, and which is useful for the diagnosis of cancer, for providing a prognosis, and for preferential targeting of a pharmacological agent to the cancer cell. Oftentimes, such markers are molecules that are overexpressed in a lung cancer or other cancer cell in comparison to a non-cancer cell, for instance, 1-fold overexpression, 2-fold overexpression, 3-fold overexpression or more in comparison to a normal cell. Further, a marker can be a molecule that is inappropriately synthesized in the cancer cell, for instance, a molecule that contains deletions, additions or mutations in comparison to the molecule expressed on a normal cell. Alternatively, such biomarkers are molecules that are underexpressed in a cancer cell in comparison to a non-cancer cell, for instance, 1-fold underexpression, 2-fold underexpression, 3-fold underexpression, or more. Further, a marker can be a molecule that is inappropriately synthesized in cancer, for instance, a molecule that contains deletions, additions or mutations in comparison to the molecule expressed on a normal cell.

It will be understood by the skilled artisan that markers may be used in combination with other markers or tests for any of the uses, e.g., prediction, diagnosis, or prognosis of cancer, disclosed herein.

"Biological sample" includes sections of tissues such as biopsy and autopsy samples, and frozen sections taken for histologic purposes. Alternatively, a biological sample can include blood and blood fractions or products (e.g., serum, plasma, platelets, red blood cells, and the like), sputum, bronchoalveolar lavage, cultured cells, e.g., primary cultures, explants, and transformed cells, stool, urine, etc. A biological sample is typically obtained from a eukaryotic organism, most preferably a mammal such as a primate e.g., chimpanzee or human; cow; dog; cat; a rodent, e.g., guinea pig, rat, Mouse; rabbit; or a bird; reptile; or fish.

A "biopsy" refers to the process of removing a tissue sample for diagnostic or prognostic evaluation, and to the tissue specimen itself. Any biopsy technique known in the art can be applied to the diagnostic and prognostic methods of the present invention. The biopsy technique applied will depend on the tissue type to be evaluated (e.g., lung etc.), the size and type of the tumor, among other factors. Representative biopsy techniques include, but are not limited to, excisional biopsy, incisional biopsy, needle biopsy, surgical biopsy, and bone marrow biopsy. An "excisional biopsy" refers to the removal of an entire tumor mass with a small margin of normal tissue surrounding it. An "incisional biopsy" refers to the removal of a wedge of tissue from within the tumor. A diagnosis or prognosis made by endoscopy or radiographic guidance can require a "core-needle biopsy", or a "fine-needle aspiration biopsy" which generally obtains a suspension of cells from within a target tissue. Biopsy techniques are discussed, for example, in *Harrison's Principles of Internal Medicine*, Kasper, et al., eds., 16th ed., 2005, Chapter 70, and throughout Part V.

The terms "overexpress," "overexpression," or "overexpressed" interchangeably refer to a protein or nucleic acid (RNA) that is translated or transcribed at a detectably greater level, usually in a cancer cell, in comparison to a normal cell. The term includes overexpression due to transcription, post transcriptional processing, translation, post-translational processing, cellular localization (e.g., organelle, cytoplasm, nucleus, cell surface), and RNA and protein stability, as compared to a normal cell. Overexpression can be detected using conventional techniques for detecting mRNA (i.e., RT-PCR, PCR, hybridization) or proteins (i.e., ELISA, immunohistochemical techniques). Overexpression can be 10%, 20%, 30%, 40%, 50%, 60%, 70%, 80%, 90% or more in comparison to a normal cell. In certain instances, overexpression is 1-fold, 2-fold, 3-fold, 4-fold or more, higher levels of transcription or translation in comparison to a normal cell.

The terms "underexpress," "underexpression," or "underexpressed" or "downregulated" interchangeably refer to a protein or nucleic acid that is translated or transcribed at a detectably lower level in a cancer cell, in comparison to a normal cell. The term includes underexpression due to transcription, post transcriptional processing, translation, post-translational processing, cellular localization (e.g., organelle, cytoplasm, nucleus, cell surface), and RNA and protein stability, as compared to a control. Underexpression can be detected using conventional techniques for detecting mRNA (i.e., RT-PCR, PCR, hybridization) or proteins (i.e., ELISA, immunohistochemical techniques). Underexpression can be 10%, 20%, 30%, 40%, 50%, 60%, 70%, 80%, 90% or less in comparison to a control. In certain instances, underexpression is 1-fold, 2-fold, 3-fold, 4-fold or more lower levels of transcription or translation in comparison to a control.

The term "differentially expressed" or "differentially regulated" refers generally to a protein or nucleic acid that is overexpressed (upregulated) or underexpressed (downregulated) in one sample compared to at least one other sample, generally in a cancer patient compared to a sample of non-cancerous tissue in the context of the present invention.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serino (S), Threonine (T); and 8) Cysteine (C), Methionine (M). See, e.g., Creighton, Proteins (1984).

The phrase "specifically (or selectively) binds" when referring to a protein, nucleic acid, antibody, or small molecule compound refers to a binding reaction that is determinative of the presence of the protein or nucleic acid, such as the differentially expressed genes of the present invention, often in a heterogeneous population of proteins or nucleic acids and other biologics. In the case of antibodies, under designated immunoassay conditions, a specified antibody may bind to a particular protein at least two times the background and more typically more than 10 to 100 times background. Specific binding to an antibody under such conditions requires an antibody that is selected for its specificity for a particular protein. For example, polyclonal antibodies can be selected to obtain only those polyclonal antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988) for a description of immunoassay formats and conditions that can be used to determine specific immunoreactivity).

The phrase "functional effects" in the context of assays for testing compounds that modulate a marker protein includes the determination of a parameter that is indirectly or directly under the influence of a biomarker of the invention, e.g., a chemical or phenotypic. A functional effect therefore includes ligand binding activity, transcriptional activation or repression, the ability of cells to proliferate, the ability to migrate, among others. "Functional effects" include in vitro, in vivo, and ex vivo activities.

By "determining the functional effect" is meant assaying for a compound that increases or decreases a parameter that is indirectly or directly under the influence of a biomarker of the invention, e.g., measuring physical and chemical or phenotypic effects. Such functional effects can be measured by any means known to those skilled in the art, e.g., changes in spectroscopic characteristics (e.g., fluorescence, absorbance, refractive index); hydrodynamic (e.g., shape), chromatographic; or solubility properties for the protein; ligand binding assays, e.g., binding to antibodies; measuring inducible markers or transcriptional activation of the marker; measuring changes in enzymatic activity; the ability to increase or decrease cellular proliferation, apoptosis, cell cycle arrest, measuring changes in cell surface markers. The functional effects can be evaluated by many means known to those skilled in the art, e.g., microscopy for quantitative or qualitative measures of alterations in morphological features, measurement of changes in RNA or protein levels for other genes expressed in placental tissue, measurement of RNA stability, identification of downstream or reporter gene expression (CAT, luciferase, β-gal, GFP and the like), e.g., via chemiluminescence, fluorescence, colorimetric reactions, antibody binding, inducible markers, etc.

"Inhibitors," "activators," and "modulators" of the markers are used to refer to activating, inhibitory, or modulating molecules identified using in vitro and in vivo assays of cancer biomarkers. Inhibitors are compounds that, e.g., bind to, partially or totally block activity, decrease, prevent, delay activation, inactivate, desensitize, or down regulate the activity or expression of cancer biomarkers. "Activators" are compounds that increase, open, activate, facilitate, enhance activation, sensitize, agonize, or up regulate activity of cancer biomarkers, e.g., agonists. Inhibitors, activators, or modulators also include genetically modified versions of cancer biomarkers, e.g., versions with altered activity, as well as naturally occurring and synthetic ligands, antagonists, agonists, antibodies, peptides, cyclic peptides, nucleic acids, antisense molecules, ribozymes, RNAi and siRNA molecules, small organic molecules and the like. Such assays for inhibitors and activators include, e.g., expressing cancer biomarkers in vitro, in cells, or cell extracts, applying putative modulator compounds, and then determining the functional effects on activity, as described above.

In some embodiments are provided a kit that includes a set of probes. A "probe" or "probes" refers to a polynucleotide that is at least eight (8) nucleotides in length and which forms a hybrid structure with a target sequence, due to complementarity of at least one sequence in the probe with a sequence in the target region. The polynucleotide can be composed of DNA and/or RNA. Probes in certain embodiments, are detectably labeled, as discussed in more detail herein. Probes can vary significantly in size. Generally, probes are, for example, at least 8 to 15 nucleotides in length. Other probes are, for example, at least 20, 30 or 40 nucleotides long. Still other probes are somewhat longer, being at least, for example, 50, 60, 70, 80, 90 nucleotides long. Yet other probes are longer still, and are at least, for example, 100, 150, 200 or more nucleotides long. Probes can be of any specific length that falls within the foregoing ranges as well. Preferably, the probe does not contain a sequence complementary to the sequence(s) used to prime for a target sequence during the polymerase chain reaction.

The terms "complementary" or "complementarity" are used in reference to polynucleotides (that is, a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Alternatively, there may be "complete" or "total" complementarity between the nucleic acids. The degree of complementarity between nucleic acid strands has significant effects on the efficiency and strength of hybridization between nucleic acid strands.

"Oligonucleotide" or "polynucleotide" refers to a polymer of a single-stranded or double-stranded deoxyribonucleotide or ribonucleotide, which may be unmodified RNA or DNA or modified RNA or DNA.

"Amplification detection assay" refers to a primer pair and matched probe wherein the primer pair flanks a region of a target nucleic acid, typically a target gene, that defines an amplicon, and wherein the probe binds to the amplicon.

A set of probes typically refers to a set of primers, usually primer pairs, and/or detectably-labeled probes that are used to detect the target genetic variations. The primer pairs are used in an amplification reaction to define an amplicon that spans a region for a target genetic variation for each of the aforementioned genes. The set of amplicons are detected by a set of matched probes. In an exemplary embodiment, the invention is a set of TaqMan™ (Roche Molecular Systems, Pleasanton, Calif.) assays that are used to detect a set of target genetic variations used in the methods of the invention.

In one embodiment, the set of probes are a set of primers used to generate amplicons that are detected by a nucleic acid sequencing reaction, such as a next generation sequencing reaction. In these embodiments, for example, Ampli SEQ™ (Life Technologies/Ion Torrent, Carlsbad, Calif.) or TruSEQ™ (Illumina, San Diego, Calif.) technology can be employed.

A modified ribonucleotide or deoxyribonucleotide refer to molecules that can be used in place of naturally occurring bases in nucleic acid and includes, but is not limited to, modified purines and pyrimidines, minor bases, convertible nucleosides, structural analogs of purines and pyrimidines, labeled, derivatized and modified nucleosides and nucleotides, conjugated nucleosides and nucleotides, sequence modifiers, terminus modifiers, spacer modifiers, and nucleotides with backbone modifications, including, but not limited to, ribose-modified nucleotides, phosphoramidates, phosphorothioates, phosphonamidites, methyl phosphonates, methyl phosphoramidites, methyl phosphonamidites, 5'-β-cyanoethyl phosphoramidites, methylenephosphonates, phosphorodithioates, peptide nucleic acids, achiral and neutral internucleotidic linkages.

"Hybridize" or "hybridization" refers to the binding between nucleic acids. The conditions for hybridization can be varied according to the sequence homology of the nucleic acids to be bound. Thus, if the sequence homology between the subject nucleic acids is high, stringent conditions are used. If the sequence homology is low, mild conditions are used. When the hybridization conditions are stringent, the hybridization specificity increases, and this increase of the hybridization specificity leads to a decrease in the yield of non-specific hybridization products. However, under mild hybridization conditions, the hybridization specificity decreases, and this decrease in the hybridization specificity leads to an increase in the yield of non-specific hybridization products.

"Stringent conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and *Current Protocols in Molecular Biology*, ed.

Hybridization between nucleic acids can occur between a DNA molecule and a DNA molecule, hybridization between a DNA molecule and a RNA molecule, and hybridization between a RNA molecule and a RNA molecule.

A "mutein" or "variant" refers to a polynucleotide or polypeptide that differs relative to a wild-type or the most prevalent form in a population of individuals by the exchange, deletion, or insertion of one or more nucleotides or amino acids, respectively. The number of nucleotides or amino acids exchanged, deleted, or inserted can be 1, 2, 3, 4, 5, 6, 7, 8, 9, 10, 11, 12, 13, 14, 15, 16, 17, 18, 19, 20 or more such as 25, 30, 35, 40, 45 or 50. The term mutein can also encompass a translocation, for example the fusion of genes encoding the polypeptides FGFR3/TACC3, RET/CCDC6, RET/ERC1, and/or TMPRss2/ERG.

"Single nucleotide polymorphism" or "SNP" refers to a DNA sequence variation that occurs when a single nucleotide (A, T, G, or C) in the genome differs between members of a biological species or paired chromosomes in a human.

In other embodiments, the two or more probes are primer pairs.

A "primer" or "primer sequence" refers to an oligonucleotide that hybridizes to a target nucleic acid sequence (for example, a DNA template to be amplified) to prime a nucleic acid synthesis reaction. The primer may be a DNA oligonucleotide, a RNA oligonucleotide, or a chimeric sequence. The primer may contain natural, synthetic, or modified nucleotides. Both the upper and lower limits of the length of the primer are empirically determined. The lower limit on primer length is the minimum length that is required to form a stable duplex upon hybridization with the target nucleic acid under nucleic acid amplification reaction conditions. Very short primers (usually less than 3-4 nucleotides long) do not form thermodynamically stable duplexes with target nucleic acid under such hybridization conditions. The upper limit is often determined by the possibility of having a duplex formation in a region other than the pre-determined nucleic acid sequence in the target nucleic acid. Generally, suitable primer lengths are in the range of about 10 to about 40 nucleotides long. In certain embodiments, for example, a primer can be 10-40, 15-30, or 10-20 nucleotides long. A primer is capable of acting as a point of initiation of synthesis on a polynucleotide sequence when placed under appropriate conditions.

The primer will be completely or substantially complementary to a region of the target polynucleotide sequence to be copied. Therefore, under conditions conducive to hybridization, the primer will anneal to the complementary region of the target sequence. Upon addition of suitable reactants, including, but not limited to, a polymerase, nucleotide triphosphates, etc., the primer is extended by the polymerizing agent to form a copy of the target sequence. The primer may be single-stranded or alternatively may be partially double-stranded.

In some embodiments there is provided a kit encompassing at least 2 primer pairs and 2 detectably labeled probes. In these non-limiting embodiments, the 2 primer pairs and/or 2 detectably labeled probes form 2 amplification detection assays.

"Detection," "detectable" and grammatical equivalents thereof refers to ways of determining the presence and/or quantity and/or identity of a target nucleic acid sequence. In some embodiments, detection occurs amplifying the target nucleic acid sequence. In other embodiments, sequencing of the target nucleic acid can be characterized as "detecting" the target nucleic acid. A label attached to the probe can include any of a variety of different labels known in the art that can be detected by, for example, chemical or physical means. Labels that can be attached to probes may include, for example, fluorescent and luminescence materials.

"Amplifying," "amplification," and grammatical equivalents thereof refers to any method by which at least a part of a target nucleic acid sequence is reproduced in a template-dependent manner, including without limitation, a broad range of techniques for amplifying nucleic acid sequences, either linearly or exponentially. Exemplary means for performing an amplifying step include ligase chain reaction (LCR), ligase detection reaction (LDR), ligation followed by Q-replicase amplification, PCR, primer extension, strand displacement amplification (SDA), hyperbranched strand displacement amplification, multiple displacement amplification (MDA), nucleic acid strand-based amplification (NASBA), two-step multiplexed amplifications, rolling circle amplification (RCA), recombinase-polymerase amplification (RPA) (TwistDx, Cambridg, UK), and self-sustained sequence replication (3SR), including multiplex versions or combinations thereof, for example but not limited to, OLA/PCR, PCR/OLA, LDR/PCR, PCR/PCR/LDR, PCR/LDR, LCR/PCR, PCR/LCR (also known as combined chain reaction-CCR), and the like. Descriptions of such techniques can be found in, among other places, Sambrook et al. Molecular Cloning, 3$^{rd}$ Edition; Ausbel et al.; PCR Primer: A Laboratory Manual, Diffenbach, Ed., Cold Spring Harbor Press (1995); The Electronic Protocol Book, Chang Bioscience (2002), Msuih et al., *J. Clin. Micro.* 34:501-07 (1996); The Nucleic Acid Protocols Handbook, R. Rapley, ed., Humana Press, Totowa, N.J. (2002).

Analysis of nucleic acid markers can be performed using techniques known in the art including, without limitation, sequence analysis, and electrophoretic analysis. Non-limiting examples of sequence analysis include Maxam-Gilbert sequencing, Sanger sequencing, capillary array DNA sequencing, thermal cycle sequencing (Sears et al., *Biotechniques*, 13:626-633 (1992)), solid-phase sequencing (Zimmerman et al., *Methods Mol. Cell Biol.*, 3:39-42 (1992)), sequencing with mass spectrometry such as matrix-assisted laser desorption/ionization time-of-flight mass spectrometry (MALDI-TOF/MS; Fu et al., *Nat. Biotechnol.*, 16:381-384 (1998)), and sequencing by hybridization. Chee et al., *Science*, 274:610-614 (1996); Drmanac et al., *Science*, 260:1649-1652 (1993); Drmanac et al., *Nat. Biotechnol.*, 16:54-58 (1998). Non-limiting examples of electrophoretic analysis include slab gel electrophoresis such as agarose or polyacrylamide gel electrophoresis, capillary electrophoresis, and denaturing gradient gel electrophoresis. Additionally, next generation sequencing methods can be performed using commercially available kits and instruments from companies such as the Life Technologies/Ion Torrent PGM or Proton, the Illumina HiSEQ or MiSEQ, and the Roche/454 next generation sequencing system.

In some embodiments, the amount of probe that gives a fluorescent signal in response to an excited light typically relates to the amount of nucleic acid produced in the amplification reaction. Thus, in some embodiments, the amount of fluorescent signal is related to the amount of product created in the amplification reaction. In such embodiments, one can therefore measure the amount of amplification product by measuring the intensity of the fluorescent signal from the fluorescent indicator.

"Detectably labeled probe" or "detector probe" refers to a molecule used in an amplification reaction, typically for quantitative or real-time PCR analysis, as well as end-point analysis. Such detector probes can be used to monitor the amplification of the target nucleic acid sequence. In some embodiments, detector probes present in an amplification reaction are suitable for monitoring the amount of amplicon(s) produced as a function of time. Such detector probes include, but are not limited to, the 5'-exonuclease assay (TAQMAN® probes described herein (see also U.S. Pat. No. 5,538,848) various stem-loop molecular beacons (see for example, U.S. Pat. Nos. 6,103,476 and 5,925,517 and Tyagi and Kramer, 1996, Nature Biotechnology 14:303-308), stemless or linear beacons (see, e.g., WO 99/21881), PNA Molecular Beacons™ (see, e.g., U.S. Pat. Nos. 6,355,421 and 6,593,091), linear PNA beacons (see, for example, Kubista et al., 2001, SPIE 4264:53-58), non-FRET probes (see, for example, U.S. Pat. No. 6,150,097), Sunrise®/Amplifluor™ probes (U.S. Pat. No. 6,548,250), stem-loop and duplex Scorpion probes (Solinas et al., 2001, Nucleic Acids Research 29:E96 and U.S. Pat. No. 6,589,743), bulge loop probes (U.S. Pat. No. 6,590,091), pseudo knot probes (U.S. Pat. No. 6,589,250), cyclicons (U.S. Pat. No. 6,383,752), MGB Eclipse™ probe (Epoch Biosciences), hairpin probes (U.S. Pat. No. 6,596,490), peptide nucleic acid (PNA) light-up probes, self-assembled nanoparticle probes, and ferrocene-modified probes described, for example, in U.S. Pat. No. 6,485,901; Mhlanga et al., 2001, Methods 25:463-471; Whitcombe et al., 1999, Nature Biotechnology. 17:804-807; Isacsson et al., 2000, Molecular Cell Probes. 14:321-328; Svanvik et al., 2000, Anal Biochem. 281:26-35; Wolffs et al., 2001, Biotechniques 766:769-771; Tsourkas et al., 2002, Nucleic Acids Research. 30:4208-4215; Riccelli et al., 2002, Nucleic Acids Research 30:4088-4093; Zhang et al., 2002 Shanghai. 34:329-332; Maxwell et al., 2002, J. Am. Chem. Soc. 124:9606-9612; Broude et al., 2002, Trends Biotechnol. 20:249-56; Huang et al., 2002, Chem. Res. Toxicol. 15:118-126; and Yu et al., 2001, J. Am. Chem. Soc 14:11155-11161.

Detector probes can also include quenchers, including without limitation black hole quenchers (Biosearch), Iowa Black (IDT), QSY quencher (Molecular Probes), and Dabsyl and Dabcel sulfonate/carboxylate Quenchers (Epoch).

Detector probes can also include two probes, wherein for example a fluor is on one probe, and a quencher is on the other probe, wherein hybridization of the two probes together on a target quenches the signal, or wherein hybridization on the target alters the signal signature via a change in fluorescence. Detector probes can also comprise sulfonate derivatives of fluorescenin dyes with $SO_3$ instead of the carboxylate group, phosphoramidite forms of fluorescein, phosphoramidite forms of CY 5 (commercially available for example from Amersham). In some embodiments, interchelating labels are used such as ethidium bromide, SYBR® Green I (Molecular Probes), and PicoGreen® (Molecular Probes), thereby allowing visualization in real-time, or end point, of an amplification product in the absence of a detector probe. In some embodiments, real-time visualization can comprise both an intercalating detector probe and a sequence-based detector probe can be employed. In some embodiments, the detector probe is at least partially quenched when not hybridized to a complementary sequence in the amplification reaction, and is at least partially unquenched when hybridized to a complementary sequence in the amplification reaction. In some embodiments, the detector probes of the present teachings have a Tm of 63-69° C., though it will be appreciated that guided by the present teachings routine experimentation can result in detector probes with other Tms. In some embodiments, probes can further comprise various modifications such as a minor groove binder (see for example U.S. Pat. No. 6,486,308) to further provide desirable thermodynamic characteristics.

In some embodiments, detection can occur through any of a variety of mobility dependent analytical techniques based on differential rates of migration between different analyte species. Exemplary mobility-dependent analysis techniques include electrophoresis, chromatography, mass spectroscopy, sedimentation, for example, gradient centrifugation, field-flow fractionation, multi-stage extraction techniques, and the like. In some embodiments, mobility probes can be hybridized to amplification products, and the identity of the target nucleic acid sequence determined via a mobility dependent analysis technique of the eluted mobility probes, as described for example in Published P.C.T. Application WO04/46344 to Rosenblum et al., and WO01/92579 to Wenz et al. In some embodiments, detection can be achieved by various microarrays and related software such as the Applied Biosystems Array System with the Applied Biosystems 1700 Chemiluminescent Microarray Analyzer and other commercially available array systems available from Affymetrix, Agilent, Illumina, and Amersham Biosciences, among others (see also Gerry et al., J. Mol. Biol. 292:251-62, 1999; De Bellis et al., Minerva Biotec 14:247-52, 2002; and Stears et al., Nat. Med. 9:14045, including supplements, 2003). It will also be appreciated that detection can comprise reporter groups that are incorporated into the reaction products, either as part of labeled primers or due to the incorporation of labeled dNTPs during an amplification, or attached to reaction products, for example but not limited to, via hybridization tag complements comprising reporter groups or via linker arms that are integral or attached to reaction products. Detection of unlabeled reaction products, for example using mass spectrometry, is also within the scope of the current teachings.

The kits of the present invention may also comprise instructions for performing one or more methods described herein and/or a description of one or more compositions or reagents described herein. Instructions and/or descriptions may be in printed form and may be included in a kit insert. A kit also may include a written description of an Internet location that provides such instructions or descriptions.

A subject sample can be any bodily tissue or fluid that includes nucleic acids from the subject. In certain embodiments, the sample will be a blood sample comprising circulating tumor cells or cell free DNA. In other embodiments, the sample can be a tissue, such as a cancerous tissue. The cancerous tissue can be from a tumor tissue and may be fresh frozen or formalin-fixed, paraffin-embedded (FFPE).

As used herein, BLCA=bladder carcinoma, BRCA=breast carcinoma, CESC=cervical cell carcinoma, COAD=colon adenocarcinoma, GBM=glioblastoma multiforme, HNSC=head and neck squamous cell carcinoma, KIRK=clear cell renal cell carcinoma, KIRP=kidney renal papillary cell carcinoma, LAML=acute myeloid leukemia, LGG=brain lower grade glioma, LIHC=liver hepatocellular carcinoma, LUAD=lung adenocarcinoma, LUSC=squamous cell lung carcinoma, OV=ovarian serous adenocarcinoma, PRAD=prostate adenocarcinoma, READ=rectal adenocarcinoma, SKCM=cutaneous melanoma, STAD=stomach adenocarcinoma, THCA=thyroid carcinoma, and UCEC=uterine corpus endometrioid carcinoma.

The disclosure provides novel associations and variants (ie, varying breakpoint locations on one or both of the partner genes) of gene fusions such as TMPRSS2/ERG, FGFR3/TACC3, RET/CCDC6 and RET/ERC1. The disclosure contemplates, isolated nucleic acid sequences of the gene fusions and sequences complementary thereto, amplicons, transcripts, as well as probes that specifically recognize the nucleic acid sequences of the gene fusions, sequences complementary thereto, amplicons, and transcripts.

In certain embodiments, the disclosure provides a set of probes that specifically recognize one or more of the gene fusions disclosed herein.

In some embodiments, the kits and assays comprise probes that specifically recognize a target, such as a gene fusion nucleic acid sequence.

In another embodiment, the disclosure provides diagnostics and treatment targets utilizing the disclosed gene fusions. The gene fusions and associated disease states provide targets for both diagnosis and treatment. For instance, the presence, absence, or increased or decreased expression of a gene fusion target can be used to diagnose a disease state. Likewise, the gene fusions can be used for targeted therapies.

Methods of diagnosing, treating, and detecting gene fusions and associated disease are further contemplated herein.

Figure 5B:
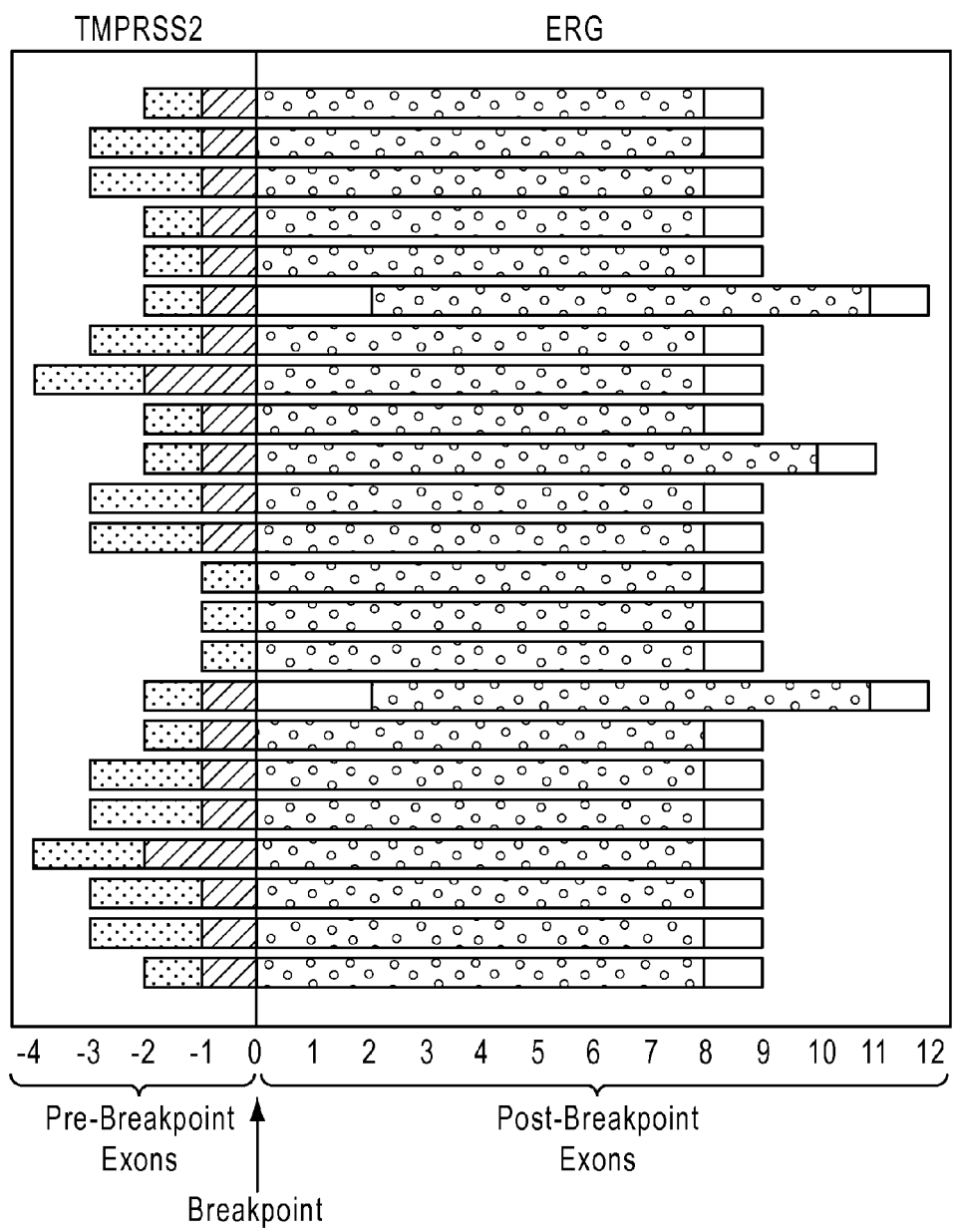
FIG. 5B shows a fused gene product exon map showing exons of each gene upstream and downstream of the breakpoint.

Transmembrane protease, serine 2 is an enzyme encoded by the TMPRSS2 gene. The TMPRSS2 protein's function in prostate cancer relies on over-expression of ETS transcription factors, such as erg, through gene fusion. Although the TMPRSS2/ERG gene fusion is known to be associated with prostate cancer, the present disclosure provides numerous novel breakpoints in each gene resulting in novel forms of the fusion. See FIG. 5. Knowing the exon location of the breakpoint in each gene is useful for detecting a gene fusion. However, the breakpoint locations in each gene (see Gene A breakpoint and Gene B breakpoint in FIG. 5A) can be used to precisely target one or more breakpoints, for primer, probe and assay design. The breakpoint variants for TMPRSS2/ERG are shown in Table 3.

Figure 6A:
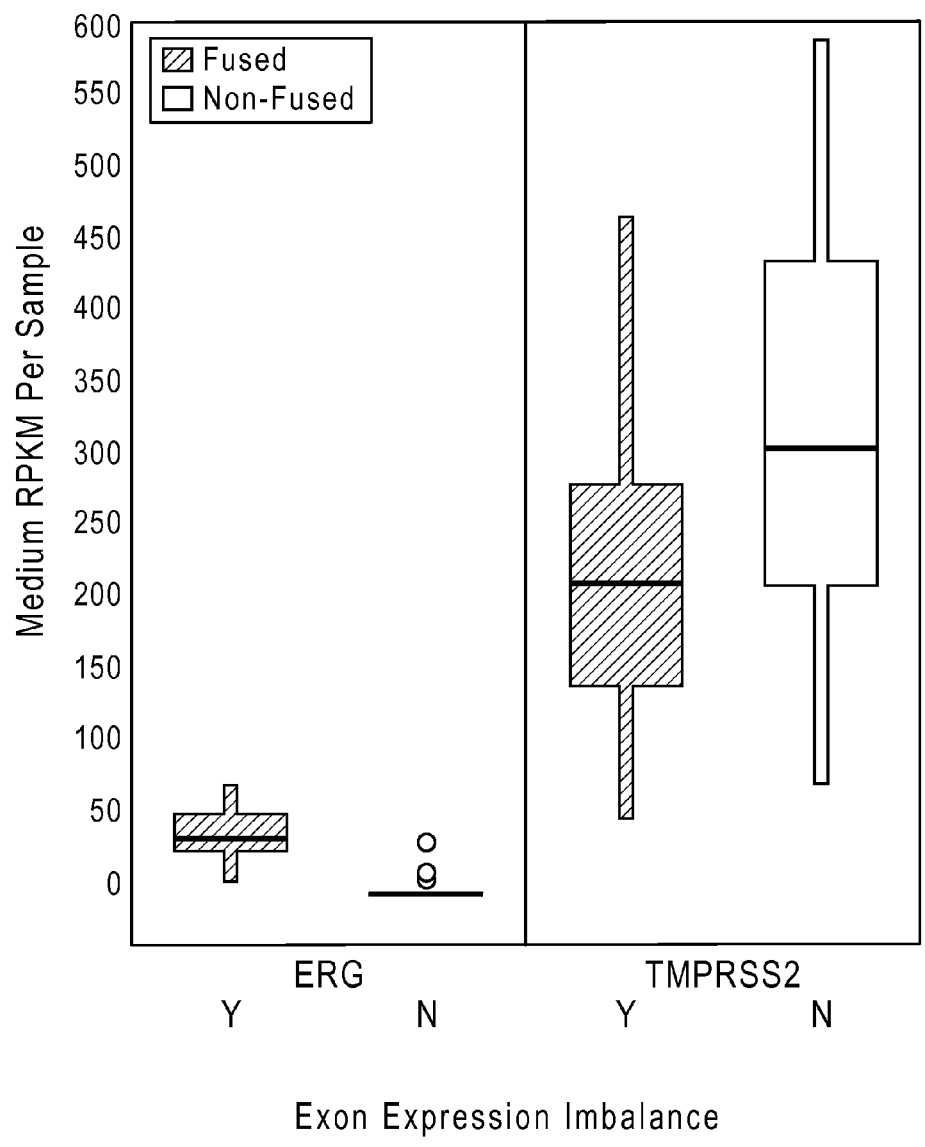
FIG. 6A is a graph of fused and non-fused samples (TMPRSS2 and ERG) exhibited exon expression imbalance prior to and after predicted fusion breakpoints. 3' partner genes of fused samples had elevated expression compared to non-fused samples.
Figure 6B:
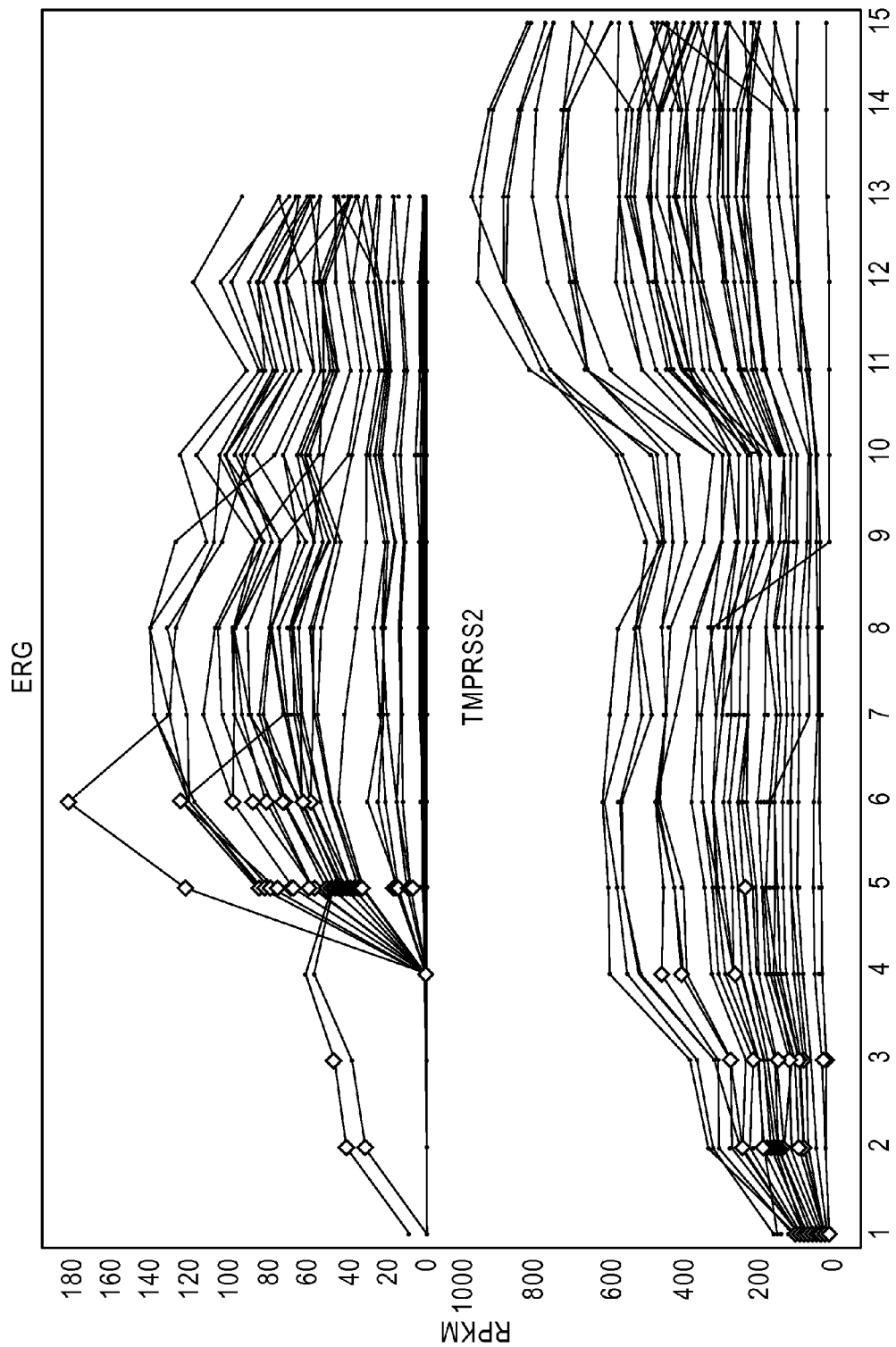
FIG. 6B is a graph of exon imbalance of ERG and TMPRSS2. 3' partner expression is impacted by the 5' partner's promoter region, then exon expression should increase post the predicted breakpoint. This effect is especially visible when viewing fused versus non-fused patient samples.
Figure 8:
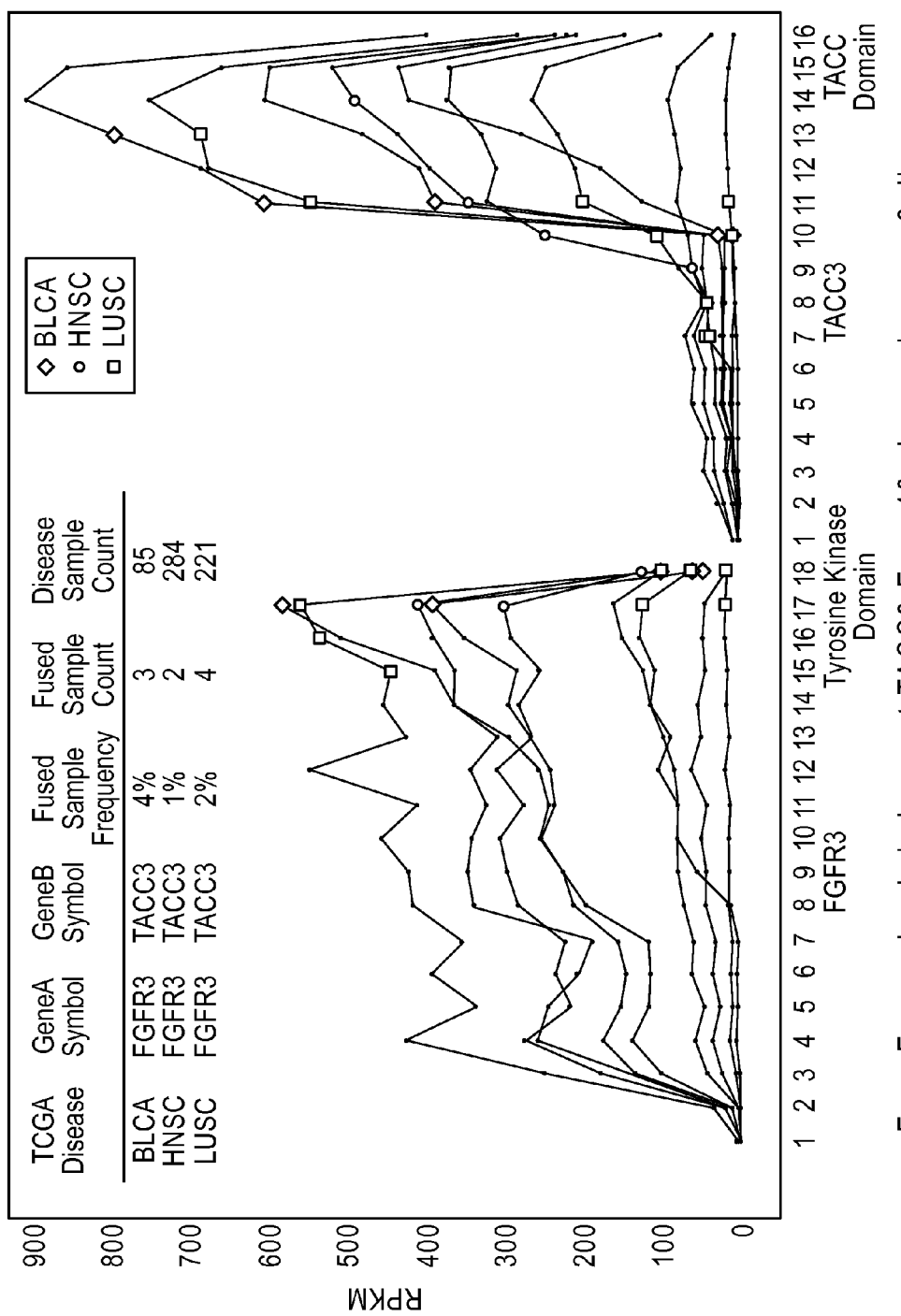
FIG. 8 shows exon expression imbalance at TACC3, exon 10 observed across bladder, head and neck, and lung squamous carcinomas.
Figure 10A:
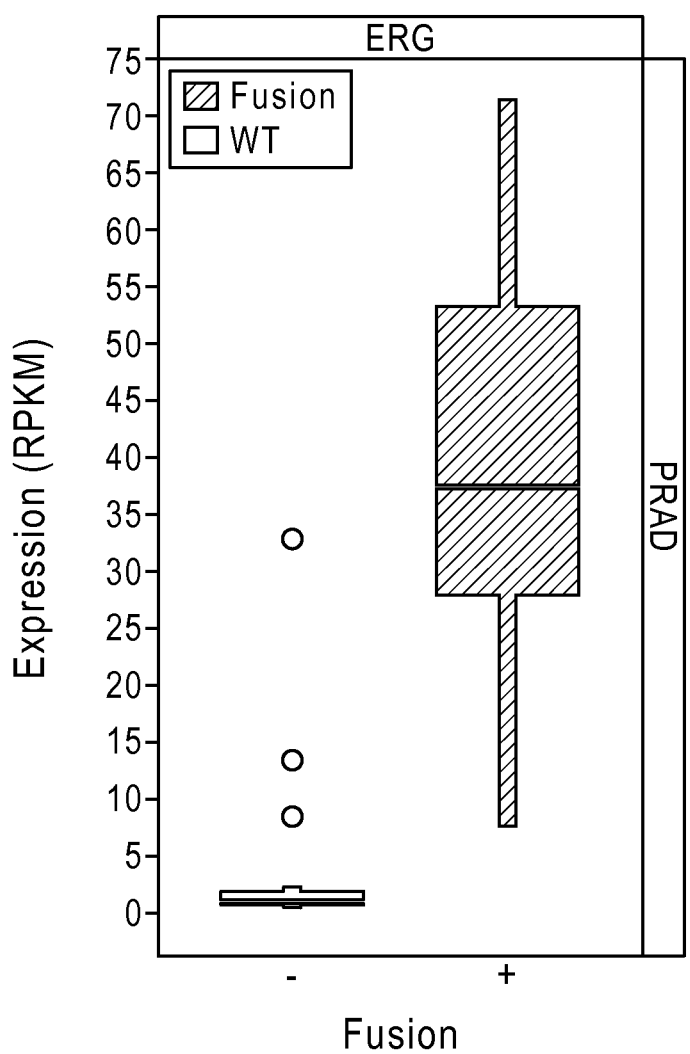
FIGS. 10A and B are graphs depicting the wild-type and predicted fusion (B) expression in PRAD (A) of TMPRSS/ERG; and exon expression v. exon boundary with predicted breakpoints in ERG.
Figure 10B:
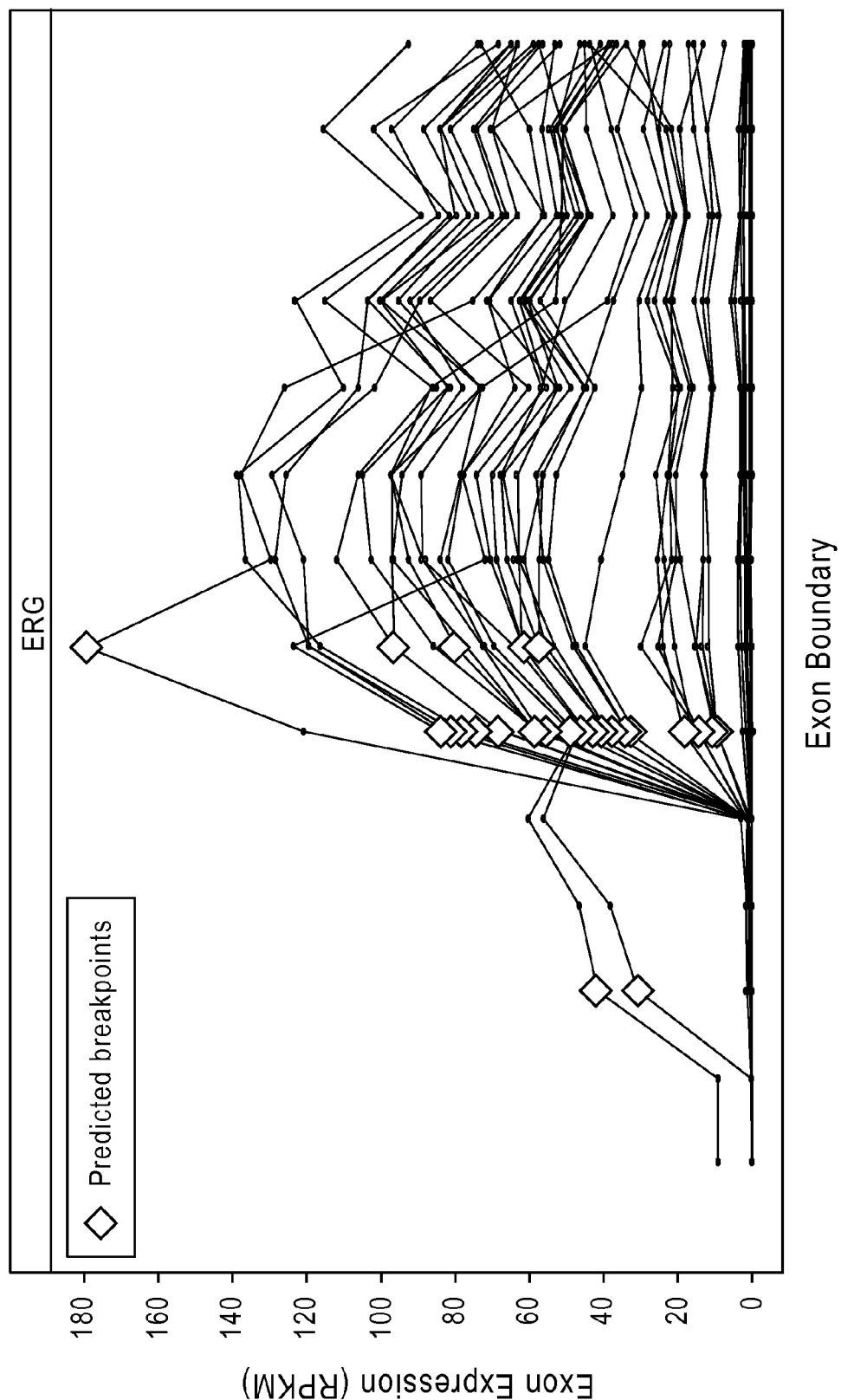
Figure 11A:
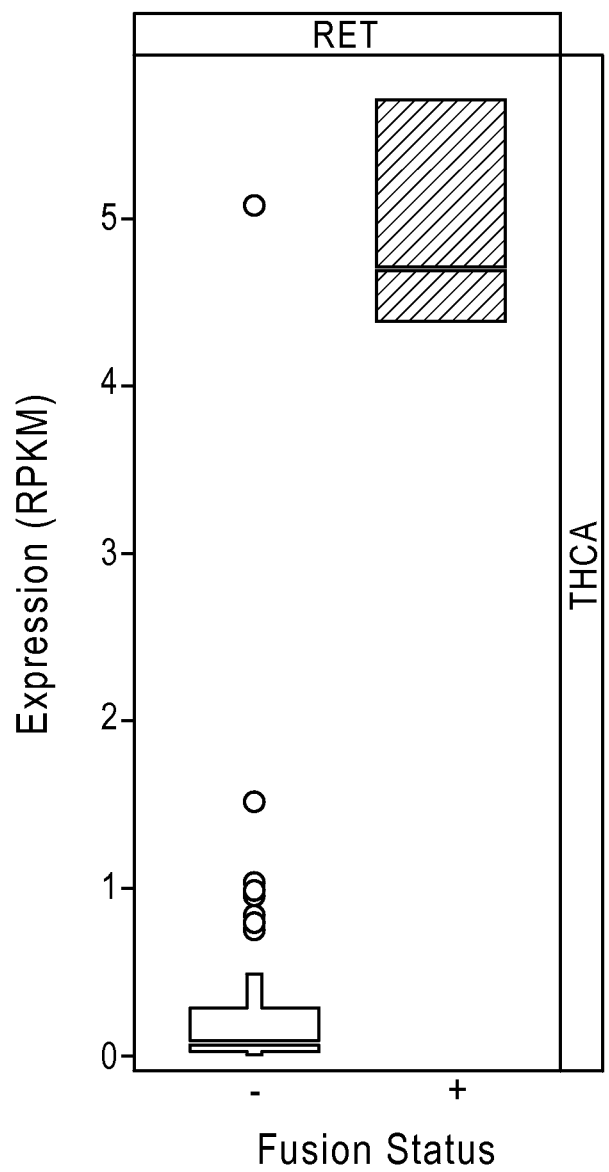
FIGS. 11A and 11B are graphs depicting the wild-type and predicted fusion expression in THCA (A) of RET (B); and exon expression v. exon boundary with predicted breakpoints in RET.
Figure 11B:
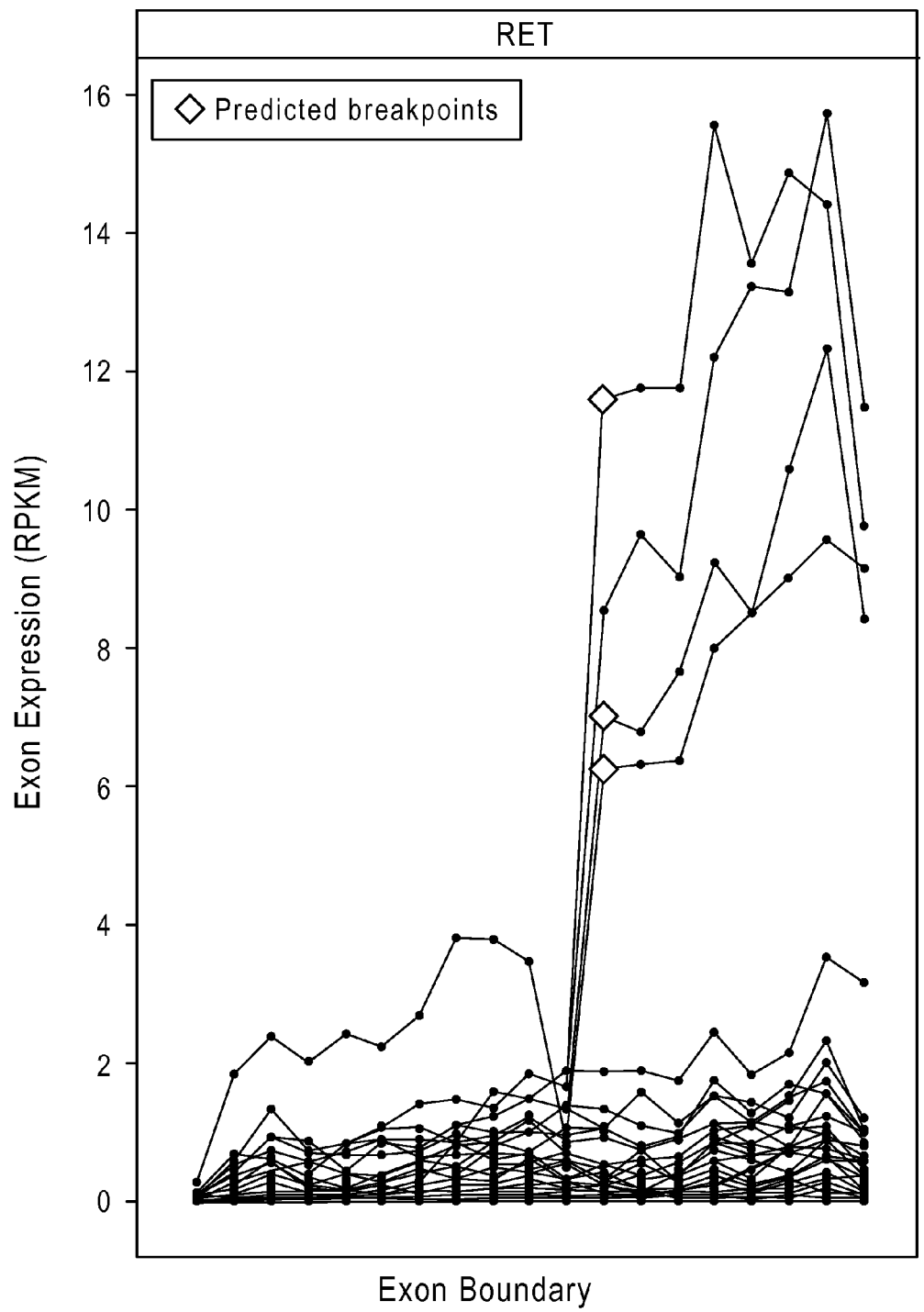
Figure 12:
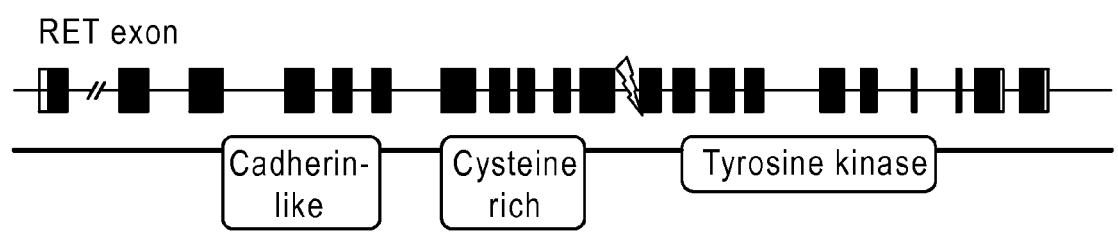
FIG. 12 is a RET exon map showing cadherin-like, cysteine rich, and tyrosine kinase domains detailed description The disclosure provides novel gene fusions and variants, as well as novel associations of the gene fusions with certain types of cancers. Further provided are probes, assays and kits using the gene fusions disclosed herein.

Exon expression of a gene fusion is altered after the breakpoint. There is an imbalance in exon expression before and after the breakpoint. This is shown for example, for the TMPRSS2/ERG fusion in FIG. 6. Exon imbalance is associated with other gene fusions disclosed herein (see also FIGS. 8 and 9).

FGFR3/TACC3 is a fusion of fibroblast growth factor receptor (FGFR3) and transforming acidic coiled-coil (TACC3) coding domains. The FGFR3/TACC3 fusion protein displays oncogenic activity. Although FGFR3/TACC3 has been previously reported, provided herein, are numerous variations of the FGFR3/TACC3 gene fusion in which the break points differ. Table 1 shows the locations for each break point in both FGFR3 and TACC3 and Table 2 provides the break point sequences (see SEQ ID NOs: 1-12).

Figure 4A:
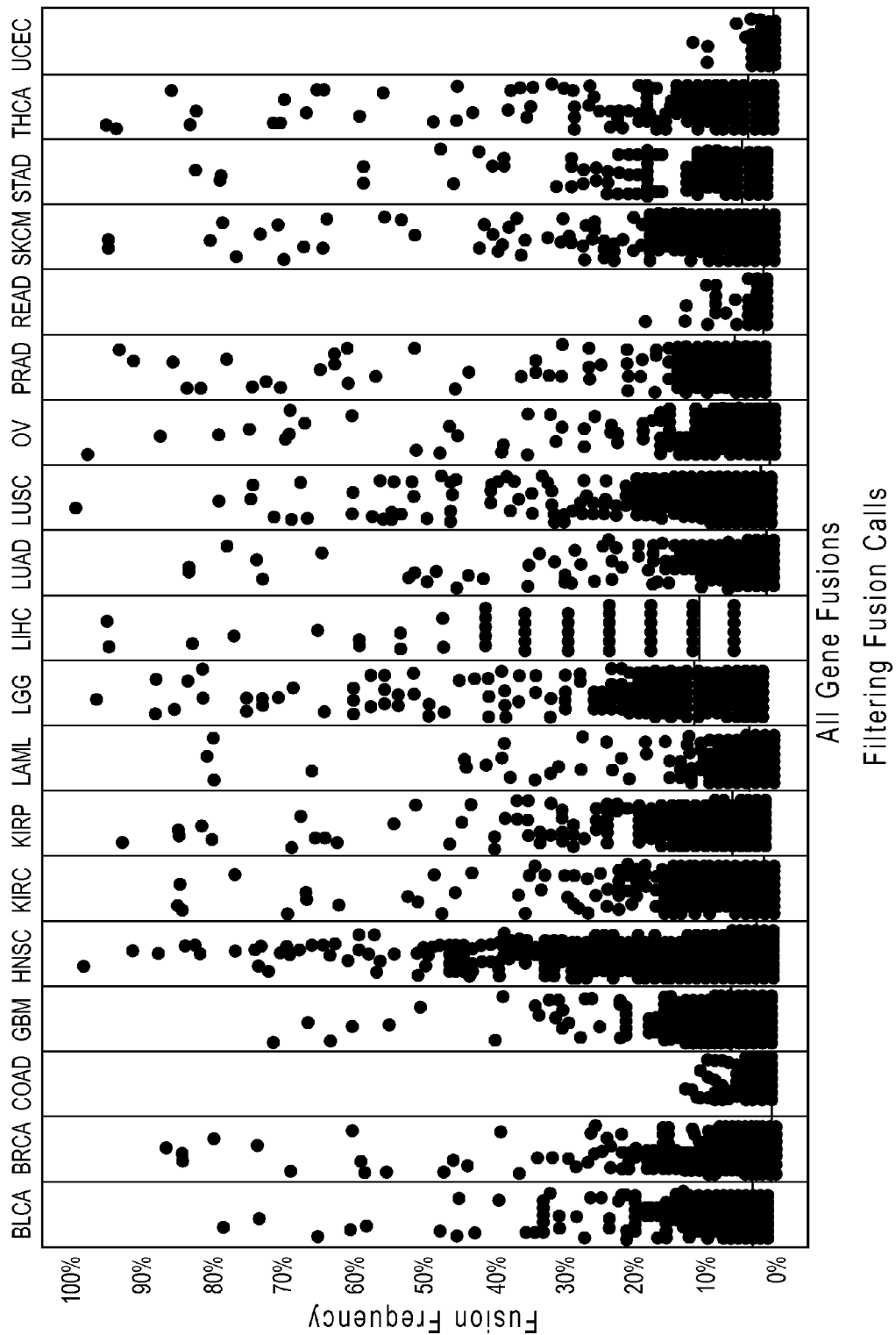
FIG. 4A shows higher frequency calls across patient populations prior to filtering.
Figure 4B:
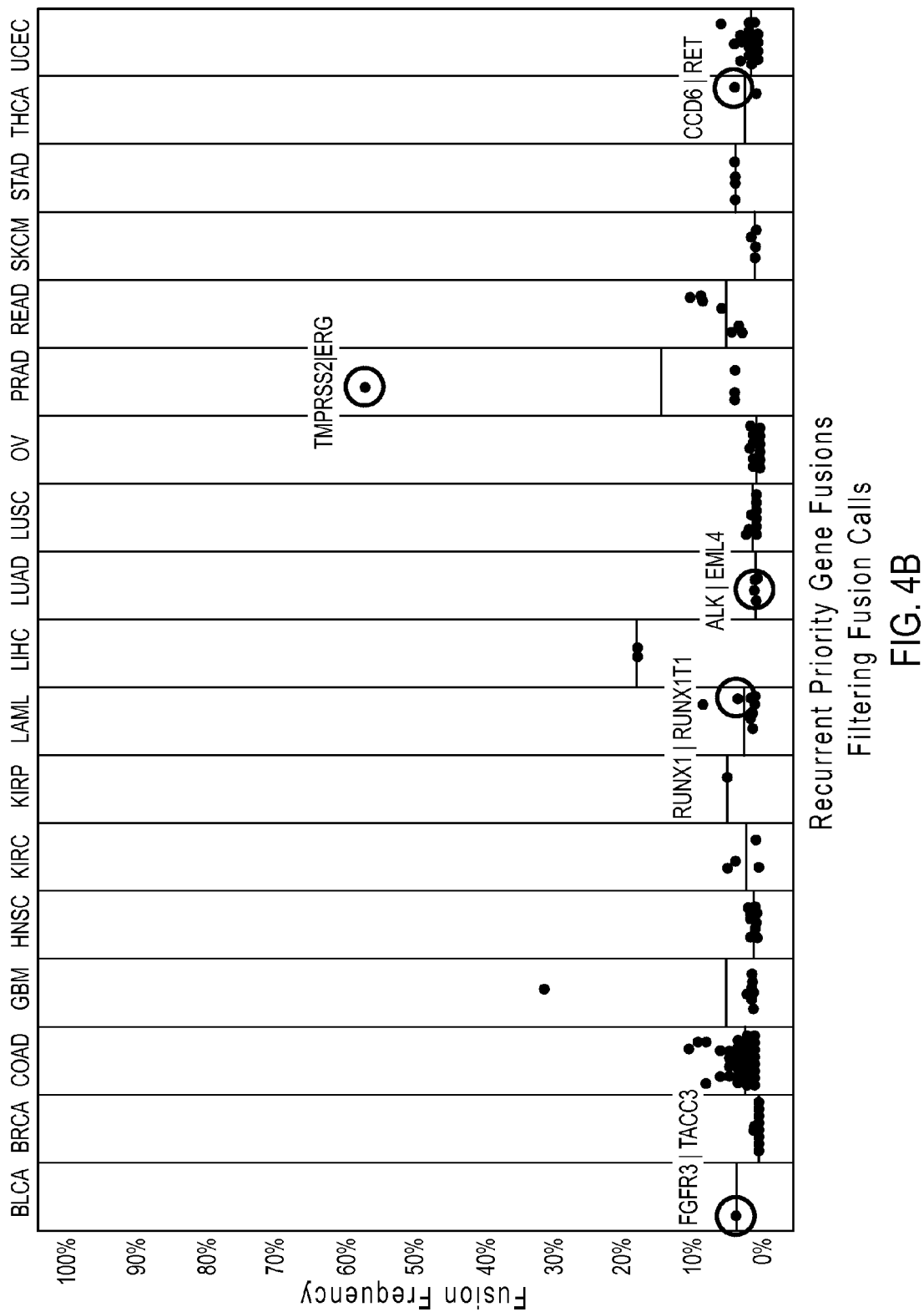
FIG. 4B is a graph showing recurrent priority gene fusions (FGFR3/TACC3, ALK/EML4, CCD6/RET, TMPRSS2/ERG) post-filtering and their frequencies in various disease states.
Figure 7:
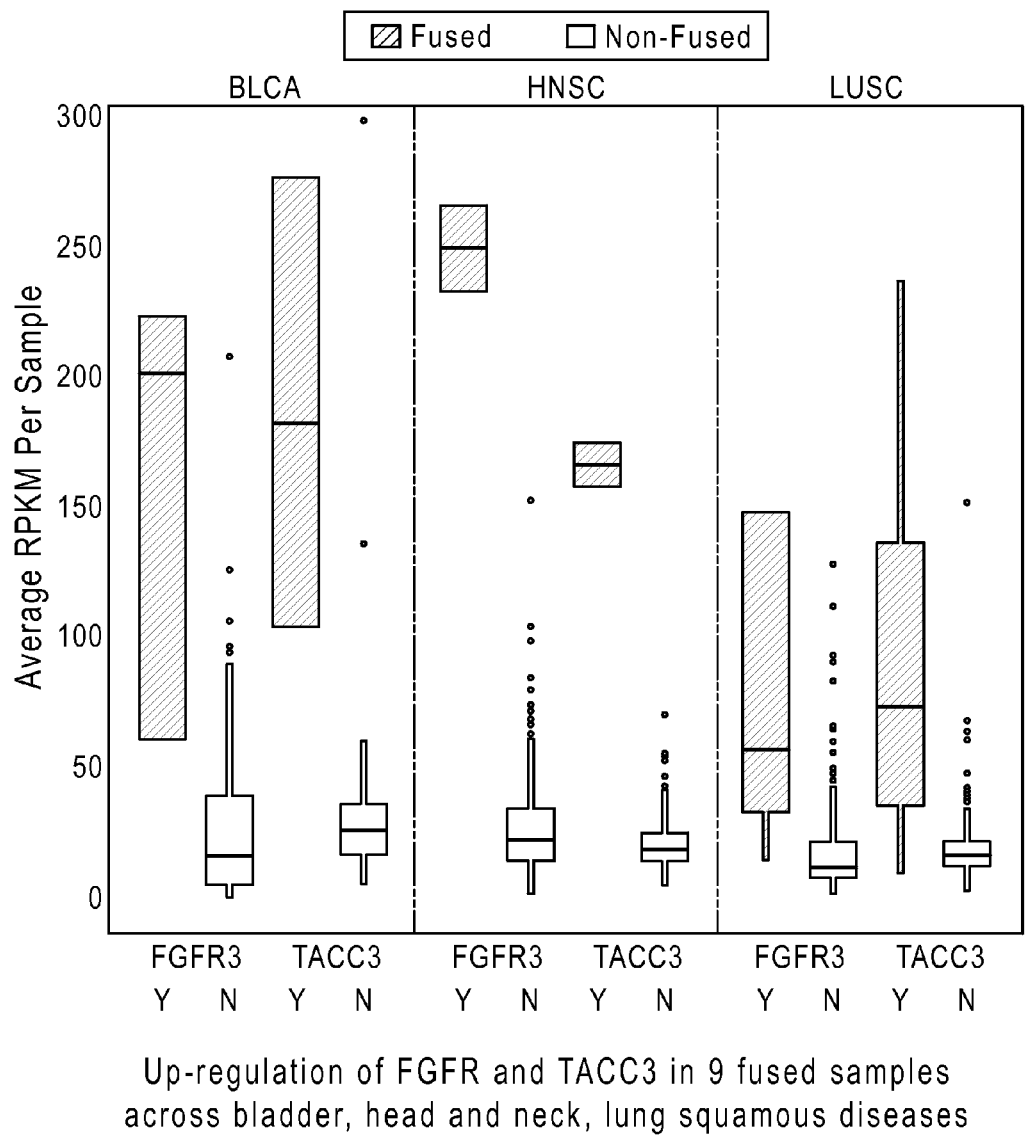
FIG. 7 is a graph showing increased expression for both fusion partners (FGFR3 and TACC3) was observed in fused samples versus non-fused samples. 9 fused samples were studied across bladder, head and neck, and lung squamous carcinomas.

The FGFR3/TACC3 fusion is known to be associated with human glioblastoma. However, as shown herein, FGFR3/TACC3 is also associated with bladder, head and neck and lung squamous cell cancers. FIGS. 4 and 7 demonstrate the presence as well as an upregulation of the FGFR3/TACC3 fusion in each of these disease states. In addition, exon expression imbalance was observed at TACC3 exon 10. It is noteworthy that the tyrosine kinase domain of FGFR3 and the TACC domain of TACC3 are preserved in the fusion. These domains are necessary for gene fusion function.

RET is a proto-oncogene located on chromosome 10 and has 21 exons. RET fusions are known in various disease states. RET fusions involve multiple partners and vary according to disease state. As shown in FIG. 9, CCDC6 and ERC1 are fusion partners of RET. In samples taken from breast, lung and thyroid cancer, RET was present in each disease state. However, only CCDC6/RET fusions were found in lung and thyroid cancer samples, whereas ERC1/RET fusions were found in breast cancer samples. In all fusions, the RET tyrosin kinase domain was preserved. Table 4 shows the breakpoints for each gene in the CCDC6/RET and ERC1/RET fusion variants.

In certain embodiments, assays and methods of detection are provided. Methods for detecting gene fusions provided herein are known in the art. As non-limiting examples, such assays can include 5' nuclease PCR assays (Applied Biosystems, Foster City, Calif.) or microarray assays (Skotheim et al., *Molecular Cancer* 2009, 8:5).

TaqMan Gene Expression Assays can be designed for a set of known fusion transcripts for quantitative analysis. Such assays are designed such that the primers and probe span the breakpoint region but are not placed directly on the breakpoint.

Computer Implemented Systems

Computer systems can be utilized to in certain embodiments of the disclosure. In various embodiments, computer system can include a bus or other communication mechanism for communicating information, and a processor coupled with bus for processing information. In various embodiments, computer system can also include a memory, which can be a random access memory (RAM) or other dynamic storage device, coupled to bus for determining base calls, and instructions to be executed by processor. Memory also can be used for storing temporary variables or other intermediate information during execution of instructions to be executed by processor. In various embodiments, computer system can further include a read only memory (ROM) or other static storage device coupled to bus for storing static information and instructions for processor. A storage device, such as a magnetic disk or optical disk, can be provided and coupled to bus for storing information and instructions.

In various embodiments, computer system can be coupled via bus to a display, such as a cathode ray tube (CRT) or liquid crystal display (LCD), for displaying information to a computer user. An input device, including alphanumeric and other keys, can be coupled to bus for communicating information and command selections to processor. Another type of user input device is a cursor control, such as a mouse, a trackball or cursor direction keys for communicating direction information and command selections to processor and for controlling cursor movement on display. This input device typically has two degrees of freedom in two axes, a first axis (i.e., x) and a second axis (i.e., y), that allows the device to specify positions in a plane.

A computer system can perform the present teachings. Consistent with certain implementations of the present teachings, results can be provided by computer system 100 in response to processor executing one or more sequences of one or more instructions contained in memory. Such instructions can be read into memory from another computer-readable medium, such as storage device. Execution of the sequences of instructions contained in memory can cause processor to perform the processes described herein. Alternatively hard-wired circuitry can be used in place of or in combination with software instructions to implement the present teachings. Thus implementations of the present teachings are not limited to any specific combination of hardware circuitry and software.

In various embodiments, the term "computer-readable medium" as used herein refers to any media that participates in providing instructions to processor for execution. Such a medium can take many forms, including but not limited to, non-volatile media, volatile media, and transmission media. Examples of non-volatile media can include, but are not limited to, optical or magnetic disks, such as storage device. Examples of volatile media can include, but are not limited to, dynamic memory, such as memory. Examples of transmission media can include, but are not limited to, coaxial cables, copper wire, and fiber optics, including the wires that comprise bus.

Common forms of non-transitory computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, any other memory chip or cartridge, or any other tangible medium from which a computer can read.

In accordance with various embodiments, instructions configured to be executed by a processor to perform a method are stored on a computer-readable medium. The computer-readable medium can be a device that stores digital information. For example, a computer-readable medium includes a compact disc read-only memory (CD-ROM) as is known in the art for storing software. The computer-readable medium is accessed by a processor suitable for executing instructions configured to be executed.

In accordance with the teachings and principles embodied in this application, methods, systems, and computer readable media that can efficiently collect, analyze, store, transfer, retrieve, and/or distribute information across multiple sites and/or entities, including genomic and/or patient information, are provided.

In one embodiment, a system is provided for determining whether one or more gene fusion and/or variant is present in a sample. The system can further determine identify a disease state, such as cancer, associated with the one or more gene fusion and/or gene variant, as well as an appropriate treatment in accordance with the mutation status. In certain embodiments, the system comprises a processor in communication with a sequencing instrument that receives sequencing data.

In some embodiments, the processor can execute one or more variant calls. In some embodiments, the processor can provide, filter, and/or annotate predictions.

EXAMPLES

A 5' nuclease assay (i.e. TaqMan assay) is designed to detect a fusion of genes FGFR3 and TACC3 using commercial assay design services (Applied Biosystems, Foster City, Calif.). (See "Gene Expression Assay Performance Guaranteed With the TaqMan® Assays QPCR Guarantee Program," White Paper available from Applied Biosystems/Life Technologies, Foster City, Calif.). For the assay design, a first primer binds to a first primer binding region of a target nucleic acid, a detector probe binds to a detector probe binding region of the target nucleic acid on one side of a fusion transcript breakpoint that is found on the target nucleic acid. A second primer binds to a second primer binding region on the other side of the fusion transcript breakpoint. The transcript breakpoint region (~10 bp), SNPs and repetitive sequences are masked before the assay is designed using the Applied Biosystems custom assay design service (Applied Biosystems, Foster City, Calif.). The first and second primers and detection probe are used in a 5' nuclease assay using standard master mix formulations and cycling conditions on commercially available real-time thermocyclers (Applied Biosystems, Foster City, Calif.).

Similar methods are used to detect TMPRSS2/ERG, CCDC6/RET, ERC1/RET, comprising varying breakpoints, including the breakpoints disclosed herein. Tables 1-4 show the breakpoints for each of these fusions.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

APPENDIX 1

TABLE 1

| TCGA Disease | GeneA Gene Symbol | GeneA Chromosome | GeneA Breakpoint | GeneB Gene Symbol | GeneB Breakpoint | Spanning Reads | Fusion Type | Distance |
|---|---|---|---|---|---|---|---|---|
| LUSC | FGFR3 | chr4 | 1808574 | TACC3 | 1741459 | 18 | Intrachromosomal | 67115 |
| GBM | FGFR3 | chr4 | 1808661 | TACC3 | 1739325 | 502 | Intrachromosomal | 69336 |
| GBM | FGFR3 | chr4 | 1808661 | TACC3 | 1741429 | 4408 | Intrachromosomal | 67232 |
| BLCA | FGFR3 | chr4 | 1808661 | TACC3 | 1741429 | 935 | Intrachromosomal | 67232 |
| HNSC | FGFR3 | chr4 | 1808661 | TACC3 | 1741429 | 81 | Intrachromosomal | 67232 |
| BLCA | FGFR3 | chr4 | 1808661 | TACC3 | 1741429 | 1796 | Intrachromosomal | 67232 |
| LUSC | FGFR3 | chr4 | 1808853 | TACC3 | 1737034 | 227 | Intrachromosomal | 71819 |
| HNSC | FGFR3 | chr4 | 1808661 | TACC3 | 1739325 | 1242 | Intrachromosomal | 69336 |
| BLCA | FGFR3 | chr4 | 1808924 | TACC3 | 1739413 | 11 | Intrachromosomal | 69511 |
| LUSC | FGFR3 | chr4 | 1808661 | TACC3 | 1741429 | 3785 | Intrachromosomal | 67232 |
| LUSC | FGFR3 | chr4 | 1808652 | TACC3 | 1737485 | 661 | Intrachromosomal | 71167 |
| LUSC | FGFR3 | chr4 | 1808651 | TACC3 | 1737484 | 369 | Intrachromosomal | 71167 |

TABLE 2

| TCGA Disease | FGFR3/TACC3 Breakpoint Sequence | SEQ ID NO: |
|---|---|---|
| LUSC | TGGACAAGCCCGCCAACTGCACACA CGACCTGTACATGATCATGCGGGAG\| CTGAGGAGCAGGTGTGAGGAGCTCC ACGGGAAGAACCTGGAACTGGGGAA | 1 |
| GBM | GCAGCTGGTGGAGGACCTGGACCGT GTCCTTACCGTGACGTCCACCGACG\| TGCCAGGCCCACCCCCAGGTGTTCC CGCGCCTGGGGGCCCACCCCTGTCC | 2 |
| GBM | GCAGCTGGTGGAGGACCTGGACCGT GTCCTTACCGTGACGTCCACCGACG\| TAAAGGCGACACAGGAGGAGAACCG GGAGCTGAGGAGCAGGTGTGAGGAG | 3 |
| BLCA | AGCAGCTGGTGGAGGACCTGGACCG TGTCCTTACCGTGACGTCCACCGAC\| GTAAAGGCGACACAGGAGGAGAACC GGGAGCTGAGGAGCAGGTGTGAGGA | 4 |
| HNSC | AGCAGCTGGTGGAGGACCTGGACCG TGTCCTTACCGTGACGTCCACCGAC\| GTAAAGGCGACACAGGAGGAGAACC GGGAGCTGAGGAGCAGGTGTGAGGA | 5 |
| BLCA | AGCAGCTGGTGGAGGACCTGGACCG TGTCCTTACCGTGACGTCCACCGAC\| GTAAAGGCGACACAGGAGGAGAACC GGGAGCTGAGGAGCAGGTGTGAGGA | 6 |
| LUSC | AGGACTGCTTCCTCAAGGCCGACTC CTTAAACGAGGAAGTTCCAAACTGC\| TCCAGGTACTCCTGCTGGCGGGAGG CGGGGTGAGCGCTGTGCCACCGAGC | 7 |
| HNSC | AGCAGCTGGTGGAGGACCTGGACCG TGTCCTTACCGTGACGTCCACCGAC\| GTGCCAGGCCCACCCCCAGGTGTTC CCGCGCCTGGGGGCCCACCCCTGTC | 8 |
| BLCA | GTACTCCCCGGGTGGCCAGGACACC CCCAGCTCCAGCTCCTCAGGGGACG\| AGGACCTGGATGCAGTGGTAAAGGC GACACAGGAGGAGAACCGGGAGCTG | 9 |

TABLE 2-continued

| TCGA Disease | FGFR3/TACC3 Breakpoint Sequence | SEQ ID NO: |
|---|---|---|
| LUSC | GCAGCTGGTGGAGGACCTGGACCGT GTCCTTACCGTGACGTCCACCGACG\| TAAAGGCGACACAGGAGGAGAACCG GGAGCTGAGGAGCAGGTGTGAGGAG | 10 |
| LUSC | CCACCTTCAAGCAGCTGGTGGAGGA CCTGGACCGTGTCCTTACCGTGACG\| TCCTTATACCTCAAGTTCGACCCCC TCCTGAGGGACAGTCCTGGTAGACC | 11 |
| LUSC | GTCTACCAGGACTGTCCCTCAGGAG GGGGTCGAACTTGAGGTATAAGGAC\| GTCACGGTAAGGACACGGTCCAGGT CCTCCACCAGCTGCTTGAAGGTGGG | 12 |

TABLE 3

| GeneA Gene Symbol | GeneA Chromosome | GeneA Breakpoint | GeneB Gene Symbol | GeneB Chromosome | GeneB Breakpoint | Spanning Reads |
|---|---|---|---|---|---|---|
| TMPRSS2 | chr21 | 42,870,046 | ERG | chr21 | 39,817,544 | 61 |
| TMPRSS2 | chr21 | 42,879,877 | ERG | chr21 | 39,956,869 | 17 |
| TMPRSS2 | chr21 | 42,880,008 | ERG | chr21 | 39,817,544 | 5 |
| TMPRSS2 | chr21 | 42,870,046 | ERG | chr21 | 39,817,544 | 75 |
| TMPRSS2 | chr21 | 42,879,877 | ERG | chr21 | 39,817,544 | 30 |
| TMPRSS2 | chr21 | 42,879,877 | ERG | chr21 | 39,817,544 | 10 |
| TMPRSS2 | chr21 | 42,870,046 | ERG | chr21 | 39,817,544 | 198 |
| TMPRSS2 | chr21 | 42,870,046 | ERG | chr21 | 39,817,544 | 52 |
| TMPRSS2 | chr21 | 42,880,008 | ERG | chr21 | 39,817,544 | 8 |
| TMPRSS2 | chr21 | 42,870,046 | ERG | chr21 | 39,817,544 | 188 |
| TMPRSS2 | chr21 | 42,879,891 | ERG | chr21 | 39,817,518 | 23 |
| TMPRSS2 | chr21 | 42,870,046 | ERG | chr21 | 39,817,544 | 59 |
| TMPRSS2 | chr21 | 42,866,283 | ERG | chr21 | 39,817,544 | 54 |
| TMPRSS2 | chr21 | 42,879,884 | ERG | chr21 | 39,870,288 | 23 |
| TMPRSS2 | chr21 | 42,880,008 | ERG | chr21 | 39,817,544 | 5 |
| TMPRSS2 | chr21 | 42,879,877 | ERG | chr21 | 39,817,544 | 9 |
| TMPRSS2 | chr21 | 42,879,877 | ERG | chr21 | 39,956,869 | 25 |
| TMPRSS2 | chr21 | 42,866,406 | ERG | chr21 | 39,817,479 | 6 |
| TMPRSS2 | chr21 | 42,879,891 | ERG | chr21 | 39,817,518 | 30 |
| TMPRSS2 | chr21 | 42,870,046 | ERG | chr21 | 39,817,544 | 42 |
| TMPRSS2 | chr21 | 42,870,046 | ERG | chr21 | 39,817,544 | 15 |
| TMPRSS2 | chr21 | 42,870,046 | ERG | chr21 | 39,817,544 | 214 |
| TMPRSS2 | chr21 | 42,879,877 | ERG | chr21 | 39,817,544 | 33 |

TABLE 4

| TCGA Disease | GeneA Gene Symbol | GeneA Chromosome | GeneA Breakpoint | GeneB Gene Symbol | GeneB Chromosome | GeneB Breakpoint | Spanning Reads |
|---|---|---|---|---|---|---|---|
| THCA | CCDC6 | chr10 | 61,665,917 | RET | chr10 | 43,610,148 | 59 |
| THCA | CCDC6 | chr10 | 61,665,897 | RET | chr10 | 43,610,044 | 16 |
| THCA | CCDC6 | chr10 | 61,665,897 | RET | chr10 | 43,610,044 | 102 |
| THCA | CCDC6 | chr10 | 61,612,343 | RET | chr10 | 43,612,054 | 71 |
| LUAD | CCDC6 | chr10 | 61,665,880 | RET | chr10 | 43,612,032 | 17 |
| THCA | CCDC6 | chr10 | 61,554,235 | RET | chr10 | 43,610,029 | 65 |
| LUAD | CCDC6 | chr10 | 61,665,880 | RET | chr10 | 43,612,032 | 8 |
| THCA | CCDC6 | chr10 | 61,665,880 | RET | chr10 | 43,610,035 | 52 |
| THCA | CCDC6 | chr10 | 61,665,897 | RET | chr10 | 43,610,044 | 85 |
| THCA | CCDC6 | chr10 | 61,665,897 | RET | chr10 | 43,610,044 | 79 |
| THCA | CCDC6 | chr10 | 61,665,880 | RET | chr10 | 43,612,032 | 71 |
| THCA | CCDC6 | chr10 | 61,612,343 | RET | chr10 | 43,612,054 | 65 |
| BRCA | ERC1 | chr12 | 1,250,953 | RET | chr10 | 43,612,032 | 17 |
| THCA | CCDC6 | chr10 | 61,612,343 | RET | chr10 | 43,612,054 | 11 |
| THCA | CCDC6 | chr10 | 61,665,897 | RET | chr10 | 43,610,044 | 117 |

What is claimed:

1. A method of detecting an FGFR3-TACC3 gene fusion comprising a sequence selected from SEQ ID NOs: 1, 7, 11, and 12 in a human tissue or blood sample from a patient having lung squamous cell carcinoma, the method comprising:

generating a reaction mixture comprising a plurality of primers that specifically hybridize to a target nucleic acid comprising a sequence selected from one or more of SEQ ID NOs: 1, 7, 11, and 12, dNTPs, UDG, and nucleic acid from the human tissue or blood sample wherein said sample comprises one or more target nucleic acid(s);

amplifying the target nucleic acid(s) using the plurality of primers, thereby producing amplicons;

sequencing the amplicons; and detecting the presence of an FGFR3-TACC3 gene fusion comprising a sequence selected from SEQ ID NOs: 1, 7, 11, and 12.

2. The method of claim 1, wherein the sample is a patient tumor sample.

3. The method of claim 2, wherein the sequencing is by next generation sequencing technology.

4. A method of detecting an FGFR3-TACC3 gene fusion comprising SEQ ID NO: 5 in a human tissue or blood sample from a patient having head and neck squamous cell carcinoma, the method comprising:
- generating a reaction mixture comprising a plurality of primers that specifically hybridize to a target nucleic acid comprising SEQ ID NO: 5, dNTPs, UDG, and nucleic acid from the human tissue or blood sample wherein said sample comprises one or more target nucleic acid(s);
- amplifying the target nucleic acid(s) using the plurality of primers, thereby producing amplicons;
- sequencing the amplicons; and
- detecting the presence of an FGFR3-TACC3 gene fusion comprising SEQ ID NO: 5.

5. The method of claim 4, wherein the sample is a patient tumor sample.

6. The method of claim 4, wherein the sequencing is by next generation sequencing technology.

7. A method of detecting an FGFR3-TACC3 gene fusion comprising SEQ ID NO: 9 in a human tissue or blood sample from a patient having bladder carcinoma, the method comprising:
- generating a reaction mixture comprising a plurality of primers that specifically hybridize to a target nucleic acid comprising SEQ ID NO: 9, dNTPs, UDG, and nucleic acid from the human tissue or blood sample wherein said sample comprises one or more target nucleic acid(s);
- amplifying the target nucleic acid(s) using the plurality of primers, thereby producing amplicons;
- sequencing the amplicons; and
- detecting the presence of an FGFR3-TACC3 gene fusion comprising SEQ ID NO: 9.

8. The method of claim 7, wherein the sample is a patient tumor sample.

9. The method of claim 7, wherein the sequencing is by next generation sequencing technology.

* * * * *

SEQUENCE LISTING

<160> NUMBER OF SEQ ID NOS: 12

<210> SEQ ID NO 1
<211> LENGTH: 100
<212> TYPE: DNA
<213> ORGANISM: Homo sapiens

<400> SEQUENCE: 1
tggacaagcc cgccaactgc acacacgacc tgtacatgat catgcgggag ctgaggagca      60
ggtgtgagga gctccacggg aagaacctgg aactggggaa                          100

<210> SEQ ID NO 2
<211> LENGTH: 100
<212> TYPE: DNA
<213> ORGANISM: Homo sapiens

<400> SEQUENCE: 2
gcagctggtg gaggacctgg accgtgtcct taccgtgacg tccaccgacg tgccaggccc      60 accccaggt gttcccgcgc ctgggggccc accctgtcc                            100

<210> SEQ ID NO 3
<211> LENGTH: 100
<212> TYPE: DNA
<213> ORGANISM: Homo sapiens

<400> SEQUENCE: 3
gcagctggtg gaggacctgg accgtgtcct taccgtgacg tccaccgacg taaaggcgac      60
acaggaggag aaccgggagc tgaggagcag gtgtgaggag                          100

<210> SEQ ID NO 4
<211> LENGTH: 100
<212> TYPE: DNA
<213> ORGANISM: Homo sapiens

<400> SEQUENCE: 4
agcagctggt ggaggacctg gaccgtgtcc ttaccgtgac gtccaccgac gtaaaggcga      60
cacaggagga gaaccgggag ctgaggagca ggtgtgagga                          100

<210> SEQ ID NO 5
<211> LENGTH: 100
<212> TYPE: DNA
<213> ORGANISM: Homo sapiens

<400> SEQUENCE: 5
agcagctggt ggaggacctg gaccgtgtcc ttaccgtgac gtccaccgac gtaaaggcga      60
cacaggagga gaaccgggag ctgaggagca ggtgtgagga                          100

<210> SEQ ID NO 6
<211> LENGTH: 100
<212> TYPE: DNA
<213> ORGANISM: Homo sapiens

<400> SEQUENCE: 6
agcagctggt ggaggacctg gaccgtgtcc ttaccgtgac gtccaccgac gtaaaggcga      60
cacaggagga gaaccgggag ctgaggagca ggtgtgagga                          100

<210> SEQ ID NO 7
<211> LENGTH: 100
<212> TYPE: DNA
<213> ORGANISM: Homo sapiens

```
<400> SEQUENCE: 7
aggactgctt cctcaaggcc gactccttaa acgaggaagt tccaaactgc tccaggtact      60
cctgctggcg ggaggcgggg tgagcgctgt gccaccgagc                          100

<210> SEQ ID NO 8
<211> LENGTH: 100
<212> TYPE: DNA
<213> ORGANISM: Homo sapiens

<400> SEQUENCE: 8
agcagctggt ggaggacctg gaccgtgtcc ttaccgtgac gtccaccgac gtgccaggcc      60
cacccccagg tgttcccgcg cctgggggcc caccccctgtc                         100

<210> SEQ ID NO 9
<211> LENGTH: 100
<212> TYPE: DNA
<213> ORGANISM: Homo sapiens

<400> SEQUENCE: 9
gtactccccg ggtggccagg acacccccag ctccagctcc tcagggacg aggacctgga      60 tgcagtggta aaggcgacac aggaggagaa ccgggagctg                          100

<210> SEQ ID NO 10
<211> LENGTH: 100
<212> TYPE: DNA
<213> ORGANISM: Homo sapiens

<400> SEQUENCE: 10
gcagctggtg gaggacctgg accgtgtcct taccgtgacg tccaccgacg taaaggcgac      60
acaggaggag aaccgggagc tgaggagcag gtgtgaggag                          100

<210> SEQ ID NO 11
<211> LENGTH: 100
<212> TYPE: DNA
<213> ORGANISM: Homo sapiens

<400> SEQUENCE: 11
ccaccttcaa gcagctggtg gaggacctgg accgtgtcct taccgtgacg tccttatacc      60
tcaagttcga ccccctcctg agggacagtc ctggtagacc                          100

<210> SEQ ID NO 12
<211> LENGTH: 100
<212> TYPE: DNA
<213> ORGANISM: Homo sapiens

<400> SEQUENCE: 12
gtctaccagg actgtccctc aggaggggt cgaacttgag gtataaggac gtcacggtaa      60
ggacacggtc caggtcctcc accagctgct tgaaggtggg                          100
```